US012661019B2

(12) United States Patent
Higgins et al.

(10) Patent No.: US 12,661,019 B2
(45) Date of Patent: Jun. 23, 2026

(54) SYSTEM FOR REPRODUCTIVE MONITORING

(71) Applicant: Medtronic, Inc., Minneapolis, MN (US)

(72) Inventors: Elise J. Higgins, St. Paul, MN (US); Yong K. Cho, Excelsior, MN (US); Richard J. O'Brien, Hugo, MN (US); David J. Miller, Austin, TX (US); Rhea M. May, Golden, CO (US); Cynthia C. Barber, Blaine, MN (US); Randal C. Schulhauser, Phoenix, AZ (US); Sarah J. Yoon, Minneapolis, MN (US); Heather I. Tuccolo, Salem, NH (US)

(73) Assignee: Medtronic, Inc., Minneapolis, MN (US)

( * ) Notice: Subject to any disclaimer, the term of this patent is extended or adjusted under 35 U.S.C. 154(b) by 535 days.

(21) Appl. No.: 18/163,175

(22) Filed: Feb. 1, 2023

(65) Prior Publication Data

US 2023/0293024 A1 Sep. 21, 2023

Related U.S. Application Data

(60) Provisional application No. 63/267,575, filed on Feb. 4, 2022.

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0537* (2013.01); *A61B 5/14532* (2013.01);
(Continued)

(58) Field of Classification Search
CPC ..... A61B 5/02055; A61B 5/296; A61B 5/389; A61B 5/28; A61B 5/0537; A61B 5/14532;
(Continued)

(56) References Cited

U.S. PATENT DOCUMENTS

| | | |
|---|---|---|
| 5,404,877 A | 4/1995 | Nolan et al. |
| 6,190,324 B1 | 2/2001 | Kieval et al. |
| (Continued) | | |

FOREIGN PATENT DOCUMENTS

| | | |
|---|---|---|
| EP | 1815784 A1 | 8/2007 |
| WO | 9958056 A1 | 11/1999 |
| (Continued) | | |

OTHER PUBLICATIONS

Allahem et al., "Automated uterine contractions pattern detection framework to monitor pregnant women with a high risk of premature labour", Informatics in Medicine Unlocked, vol. 20, No. 100404, Elsevier, Jan. 29, 2020, 14 pp., URL: https://www.sciencedirect.com/science/article/pii/S2352914820305542?via%3Dihub.

(Continued)

*Primary Examiner* — Amanda L Steinberg
(74) *Attorney, Agent, or Firm* — Shumaker & Sieffert, P.A.

(57) ABSTRACT

A system for sensing one or more physiological traits and obstetric conditions, such as a fertility phase, pregnancy, labor, post-partum conditions, and other conditions related to the reproductive system of the patient. The system may use the one or more physiological traits sensed to define one or more patient attributes for the patient, such as a hormone level, heart rate, blood pressure, respiration rate, temperature, oxygen saturation level, uterine contractions, fluid level, and/or other patient attributes. The system is config- (Continued)

ured to compare the one or more patient attributes to one or more attribute signs describing a threshold for the one or more patient attributes. The system is configured to issue a communication to the patient and/or a clinician based on the comparisons. The system may be configured to assess and indicate reproductive phases for the patient over a life-cycle from the fertility phase to the post-partum phase.

17 Claims, 9 Drawing Sheets

(51) Int. Cl.

| | |
|---|---|
| A61B 5/021 | (2006.01) |
| A61B 5/0245 | (2006.01) |
| A61B 5/0537 | (2021.01) |
| A61B 5/08 | (2006.01) |
| A61B 5/145 | (2006.01) |
| A61B 5/1455 | (2006.01) |
| A61B 5/28 | (2021.01) |
| A61B 5/296 | (2021.01) |
| A61B 5/389 | (2021.01) |
| A61B 10/00 | (2006.01) |

(52) U.S. Cl.
CPC ............ *A61B 5/14551* (2013.01); *A61B 5/28* (2021.01); *A61B 5/296* (2021.01); *A61B 5/389* (2021.01); *A61B 5/4227* (2013.01); *A61B 5/4356* (2013.01); *A61B 5/7475* (2013.01); *A61B 10/0012* (2013.01); *A61B 5/021* (2013.01); *A61B 5/0245* (2013.01); *A61B 5/0816* (2013.01)

(58) Field of Classification Search
CPC . A61B 5/14551; A61B 5/4227; A61B 5/4356; A61B 5/7475; A61B 5/021; A61B 5/0245; A61B 5/0816; A61B 10/0012
See application file for complete search history.

(56) References Cited

U.S. PATENT DOCUMENTS

| | | | |
|---|---|---|---|
| 6,312,378 | B1 | 11/2001 | Bardy |
| 6,409,675 | B1 | 6/2002 | Turcott |
| 6,438,407 | B1 | 8/2002 | Ousdigian et al. |
| 6,582,365 | B1 | 6/2003 | Hines et al. |
| 7,188,151 | B2 | 3/2007 | Kumar et al. |
| 7,653,434 | B1 | 1/2010 | Turcott et al. |
| 8,043,213 | B2 | 10/2011 | Hatlestad et al. |
| 9,186,089 | B2 | 11/2015 | Mazar et al. |
| 10,172,593 | B2 | 1/2019 | Shinar et al. |
| 10,278,581 | B2 | 5/2019 | Gaster |
| 10,413,200 | B2 | 9/2019 | Joseph |
| 10,413,207 | B2 | 9/2019 | Sarkar et al. |
| 10,420,476 | B2 | 9/2019 | Moon et al. |
| 10,610,150 | B2 | 4/2020 | Berry |
| 2004/0100376 | A1 | 5/2004 | Lye et al. |
| 2004/0122487 | A1 | 6/2004 | Hatlestad et al. |
| 2007/0016089 | A1 | 1/2007 | Fischell et al. |
| 2008/0319353 | A1 | 12/2008 | Howell et al. |
| 2010/0268095 | A1 | 10/2010 | Mazar et al. |
| 2013/0053657 | A1 | 2/2013 | Ziarno et al. |
| 2016/0058429 | A1* | 3/2016 | Shinar .................. A61B 5/4809 |
| | | | 600/551 |
| 2016/0066894 | A1 | 3/2016 | Barton-Sweeney |
| 2016/0174840 | A1 | 6/2016 | Udoh et al. |
| 2016/0374608 | A1 | 12/2016 | Dugan |
| 2017/0224268 | A1* | 8/2017 | Altini .................. A61B 5/4362 |
| 2017/0265807 | A1 | 9/2017 | Stopek |
| 2017/0281001 | A1 | 10/2017 | Stopek |
| 2019/0090742 | A1 | 3/2019 | Hahn et al. |
| 2019/0090743 | A1 | 3/2019 | Hahn et al. |
| 2019/0150776 | A1 | 5/2019 | Bardy et al. |
| 2019/0167139 | A1 | 6/2019 | Bardy |
| 2020/0000441 | A1* | 1/2020 | Lafon ................ A61B 5/02438 |
| 2020/0072782 | A1 | 3/2020 | Hanh et al. |
| 2020/0086110 | A1 | 3/2020 | Karsdon et al. |
| 2020/0113470 | A1 | 4/2020 | Friedman et al. |
| 2020/0196958 | A1 | 6/2020 | Penders et al. |
| 2020/0222032 | A1 | 7/2020 | Stein |
| 2020/0229800 | A1* | 7/2020 | Mena Benito ..... A61B 10/0012 |
| 2021/0113099 | A1 | 4/2021 | Rogers et al. |
| 2021/0162125 | A1 | 6/2021 | Altschul et al. |
| 2021/0257091 | A1* | 8/2021 | Spang .................. A61B 5/4842 |
| 2021/0378585 | A1 | 12/2021 | Daniele et al. |

FOREIGN PATENT DOCUMENTS

| | | | |
|---|---|---|---|
| WO | | 2020194350 A1 | 10/2020 |
| WO | | 2020243463 A1 | 12/2020 |
| WO | | 2021050818 A1 | 3/2021 |

OTHER PUBLICATIONS

Arizton, "Maternity Care Market—Global Outlook and Forecast 2017-2023", Arizton Advisory & Intelligence, 5 pp., Retrieved from the Internet on Apr. 13, 2023 from URL: https://www.arizton.com/market-reports/maternity-care-market#snapshots.

Bezemer et al., "Simultaneous multi-depth assessment of tissue oxygen saturation in thenar and forearm using near- Infrared spectroscopy during a simple cardiovascular challenge", Crit Care, vol. 13, No. 5, Nov. 30, 2009, 5 pp., URL: https://ccforum.biomedcentral.com/articles/10.1186/cc8003.

Clifford, "Chapter 15—Blind Source Separation: Principal & Independent Component Analysis", Biomedical Signal and Image Processing, 2008, pp. 1-47, Retrieved from the Internet on Apr. 13, 2023 from URL: http://www.mit.edu/~gari/teaching/6.555/LECTURE_NOTES/ch15_bss.pdf.

Fotiadou et al., "Multi-Channel Fetal ECG Denoising With Deep Convolutional Neural Networks", Frontiers in Pediatrics, vol. 8, No. 508, Aug. 26, 2020, 13 pp., URL: https://www.frontiersin.org/articles/10.3389/fped.2020.00508/full.

Garcia-Canadilla et al., "Machine Learning in Fetal Cardiology: What to Expect", Fetal Diagnosis and Therapy, vol. 47, No. 5, Jan. 7, 2020, pp. 363-372, URL: https://pubmed.ncbi.nlm.nih.gov/31910421/.

GE Healthcare, "Monica Novii Wireless Patch System: Empowering you and your patients", General Electric Company, 2018, 8 pp., Retrieved from the Internet on Apr. 13, 2023 from URL: https://www.womens-health.net/data/files/mic-eu-novii-wireless-patch-system-brochure-english-04-2018-jb25922us3a.pdf.

Hines et al., "Biotelemetry Using Implanted Unit To Monitor Preterm Labor", Tech Briefs Engineering Solutions for Design & Manufacturing, May 1, 1999, 5 pp., URL: https://www.techbriefs.com/component/content/article/tb/pub/briefs/electronics-and-computers/1837.

International Search Report and Written Opinion of International Application No. PCT/IB2023/050916 dated May 4, 2023, 13 pp.

Martin et al., "National Vital Statistics Reports", CDC, vol. 68, No. 13, Nov. 30, 2019, 47 pp., URL: https://www.cdc.gov/nchs/data/nvsr/nvsr68/nvsr68_13-508.pdf.

Medtech Innovator, "Tiny Kicks", 1 pp., Retrieved from the Internet on Apr. 13, 2023 from URL: https://medtechinnovator.org/company/tinykicks/.

Pal et al., "Blind Source Separation: A Review and Analysis", 2013 International Conference Oriental COCOSDA held jointly with 2013 Conference on Asian Spoken Language Research and Evaluation, IEEE, Nov. 25, 2013, 5 pp., URL: https://ieeexplore.ieee.org/abstract/document/6709849.

Raydiant Oximetry, Inc, "Raydiant Oximetry", 5 pp., Retrieved from the Internet on Apr. 13, 2023 from URL: https://www.raydiantoximetry.com/.

The Femtech Focus et al., "The FemTech Focus Podcast with Dr. Brittany Barreto", FemHealth Insights, 12 pp., Retrieved from the

(56)     References Cited

OTHER PUBLICATIONS

Internet on May 1, 2023 from URL: https://www.femtechfocus.com/.

* cited by examiner

SENSING ONE OR MORE PHYSIOLOGICAL TRAITS OF A PATIENT — 902

RECEIVING, BY PROCESSING CIRCUITRY, AN OUTPUT SIGNAL — 904

DEFINING, USING PROCESSING CIRCUITRY, A PATIENT ATTRIBUTE — 906

ISSUING A COMMUNICATION BASED ON THE PATIENT ATTRIBUTE — 908

SYSTEM FOR REPRODUCTIVE MONITORING

This application claims the benefit of U.S. Provisional Patent Application Ser. No. 63/267,575 (filed Feb. 4, 2022), which is entitled, "SYSTEM FOR REPRODUCTIVE MONITORING" and is incorporated by reference herein in its entirety.

TECHNICAL FIELD

This disclosure generally relates to systems including medical devices and, more particularly, to monitoring of patients during conception, gestation, labor, delivery, and post-partum using such systems.

BACKGROUND

Reproductive system checkups are periodically conducted during and/or before conception, gestational, delivery, and post-partum periods to evaluate the health and progress of a maternal patient and/or a fetal patient. During the checkup, a clinician may evaluate various physiological traits to assess fertility, conception, pregnancy, post-partum health, and other wellness aspects of the patient. Similarly, a patient may conduct self-evaluations to assess fertility, conception, pregnancy, post-partum health, and other wellness aspects. The indications observed may be generally tracked to assess, for example, ovulation, conception, maternal and/or fetal health during pregnancy, indications of delivery, post-partum conditions, and other health aspects related to the reproductive system of the patient. In some cases, the physiological traits of the patient are obtained and assessed using medical equipment located within a medical clinic, requiring a physical presence of the patient. In some cases, the physiological traits are obtained and assessed by the patient, placing a tracking and/or evaluation burden on the patient outside of a medical clinic setting.

SUMMARY

In general, the disclosure describes a system configured to sense one or more physiological traits of a patient to monitor and/or assess a likelihood of obstetric conditions in the patient, such as an obstetric condition indicative of a fertility phase, pregnancy, labor, post-partum conditions, and other conditions related to the reproductive system of the patient. The system is configured to sense one or more of the physiological traits using one or more sensors implanted subcutaneously and/or positioned cutaneously on the skin, or other sensors accessible to the patient outside of a medical clinic environment. The system may use the one or more physiological traits sensed to define one or more patient attributes for the patient, such as a hormone level, heart rate, blood pressure, respiration rate, temperature, oxygen saturation level, uterine contractions, fluid level, and/or other patient attributes. The system is configured to compare the one or more patient attributes to an attribute sign describing a threshold for the one or more patient attributes. The system is configured to generate an indication for output (e.g., issue a communication or alert) to the patient and/or a clinician based on the comparisons. In examples, the system regularly or asynchronously communicates the one or more patient attributes to an output device of the maternal patient, interested participants (e.g., a co-parent), and/or a clinician, such that the maternal patient, interested participants (e.g., a co-parent), and/or the clinician may remain updated on the various attributes without requiring a physical presence within the medical clinic. Hence, the system may provide indications to the patient and/or a clinician when the physiological traits obtained indicate the patient may be experiencing a fertility phase (e.g., menses, a follicular phase, ovulation, a luteal phase), pregnant, in labor, or experiencing a concerning post-partum condition. The system may thus be configured to assess and indicate reproductive phases for the patient over a life-cycle from the fertility phase to the post-partum phase.

The system may include sensing circuitry operably connected to the one or more sensors. The sensing circuitry may be configured to communicate one or more output signals indicative of the physical traits sensed to processing circuitry operably connected to the sensing circuitry. The processing circuitry may define the one or more patient attributes using the one or more output signals. The processing circuitry issue the communication based on a comparison of one or more of the one or more patient attributes with one or more of the one or more attribute signs. The one or more attribute signs may describe a threshold for one or more of the one or more patient attributes.

The system provides for scheduled monitoring (e.g., continuously, hourly, twice per day, or some other schedule) using one or more sensors implanted in and/or wearable by the patient. Hence, the system may communicate sensed physiological traits and/or patient attributes more frequently and on a more consistent schedule than might otherwise be available when monitoring requires presence with a medical facility setting and/or a concerted action by the patient. Further, the sensed patient data and/or prior patient data may be provided to and/or evaluated by a clinician in a more expeditious and consistent manner. In examples, the system is configured to alter its operation based on prior patient data and/or an input received from a clinician IO device. For example, the system may increase or decrease a frequency at which a sensor or group of sensors senses a particular patient physical trait and/or one or more physiological traits sensed by the system, a scheduled basis for providing patient physiological data, one or more patient attributes used by the system, one or more attribute signs, and/or other operations. Thus, the system may update and/or adjust monitoring of a patient without a necessity for physical visitation to a medical facility and/or with a clinician.

The use of a patient attribute based on one or more physiological traits sensed from the patient may enhance the detection of obstetric conditions such as a fertility phase, pregnancy, labor, post-partum conditions, and others as the patient experiences the reproductive cycle. Typical monitoring of patients generally occurs by sensing and evaluating patient physiological traits often individually and/or largely within the setting of a medical facility. Example systems disclosed herein may monitor and define a patient attribute using a combination of physiological traits, and further compare the physiological trait to an attribute sign which considers the combined physiological traits.

In examples, the system uses a machine learning algorithm to improve monitoring and/or indications provided to the patient and/or a clinician. The machine learning algorithm may assist in interpreting patient attributes to, for example, identify whether an obstetric condition (e.g., a fertility phase, pregnancy, labor, post-partum) may be present for the patient. For example, processing circuitry of the system may be configured to train the machine learning algorithm using prior patient data sensed for the patient, such that an attribute sign is based at least in part on physiological traits somewhat specific to the patient rather than, for example, based broadly on other metrics which may be relatively insensitive to the specific physiological traits of an individual patient. In examples, the system may incorporate prior patient data obtained by the system to evaluate and/or update attribute signs. Hence, the machine learning algorithm may allow the system to provide substantially personalized interpretations, evaluations, and/or communications specific to the individual physiological traits exhibited by the patient. Implementing such personalized approaches in the systems and techniques described herein realize an increase in accuracy for detecting true episodes, for instance, by detecting fewer false positives and overlooking fewer false negatives for obstetric conditions that may be present in the patient.

The system may improve identification and/or responsiveness to trends and/or indications which might emerge from physiological data collected from a population of users. The system may assist in defining a patient attribute and/or attribute sign, a schedule for sensing physiological traits, and/or other operations based on the population data. For example, the machine learning algorithm may define and/or refine an attribute sign using population data sensed from a population of other individual patients. The machine learning algorithm may be trained using a training data set including the population data. In examples, the system is configured to communicate with a plurality of individual medical devices worn, implanted within, and/or otherwise utilized by the population of other individual patients. The medical system may communicate with the plurality of individual medical devices to gather the population data. Hence, the machine learning algorithm may allow the system to more rapidly respond to the identification of and use of trends that might emerge as a result of monitoring a broad population of patients.

The techniques and systems of this disclosure may be implemented in a medical device such as an implantable medical device (IMD) that can continuously (e.g., on a periodic or triggered basis without human intervention) sense physiological traits while being worn or subcutaneously implanted in a patient over months or years, and perform numerous operations per second on patient data to enable the systems herein to detect potential obstetric conditions. Using techniques of this disclosure with a medical device such as an IMD may be advantageous when a physician cannot be continuously present with the patient over weeks or months to evaluate physiological traits sensed by the system, and/or where performing the operations of the system on the physiological traits (e.g., personalization of maternal and/or fetal limits, incorporation of trends identified from population data) on weeks or months of data gathered through physiological monitoring could not practically be performed in the mind of a physician.

In an example, a system comprises: one or more sensors configured to sense one or more physiological traits indicative of one or more patient attributes of a patient, wherein the one or more patient attributes are indicative of one or more physiological characteristics of a body of the patient; sensing circuitry operably connected to the one or more sensors and configured to issue one or more output signals indicative of the one or more physiological trait; and processing circuitry operably connected to the sensing circuitry, wherein the processing circuitry is configured to: receive the one or more output signals from the sensing circuitry, define the one or more patient attributes using the one or more received output signals, and issue a communication based on a comparison of the one or more patient attributes and an attribute sign, wherein the attribute sign defines a threshold for the patient attribute, wherein the attribute sign is indicative of an obstetric condition defined by the one or more of the physiological characteristics, and wherein the obstetric condition is indicative of a fertility phase of the patient, a pregnancy of the patient, labor of the patient, or a post-partum condition of the patient.

In an example, a method comprises: sensing one or more physiological traits indicative of one or more patient attributes of a patient using one or more sensors, wherein the one or more patient attribute is indicative of one or more physiological characteristics of a body of the patient; receiving, by processing circuitry, one or more output signals generated by sensing circuitry operably connected to the one or more sensors, wherein the one or more output signals are indicative of the one or more patient attributes; defining, using the processing circuitry, the one or more patient attributes using the one or more received output signals; and issuing a communication, using the processing circuitry, based on a comparison of the one or more patient attributes and an attribute sign, wherein the attribute sign defines a threshold for the patient attribute, wherein the attribute sign is indicative of an obstetric condition defined by the one or more of the physiological characteristics, and wherein the obstetric condition is indicative of a fertility phase of the patient, a pregnancy of the patient, labor of the patient, or a post-partum condition of the patient.

The details of one or more examples are set forth in the accompanying drawings and the description below. Other features, objects, and advantages will be apparent from the description and drawings, and from the claims.

DETAILED DESCRIPTION

Figure 1:
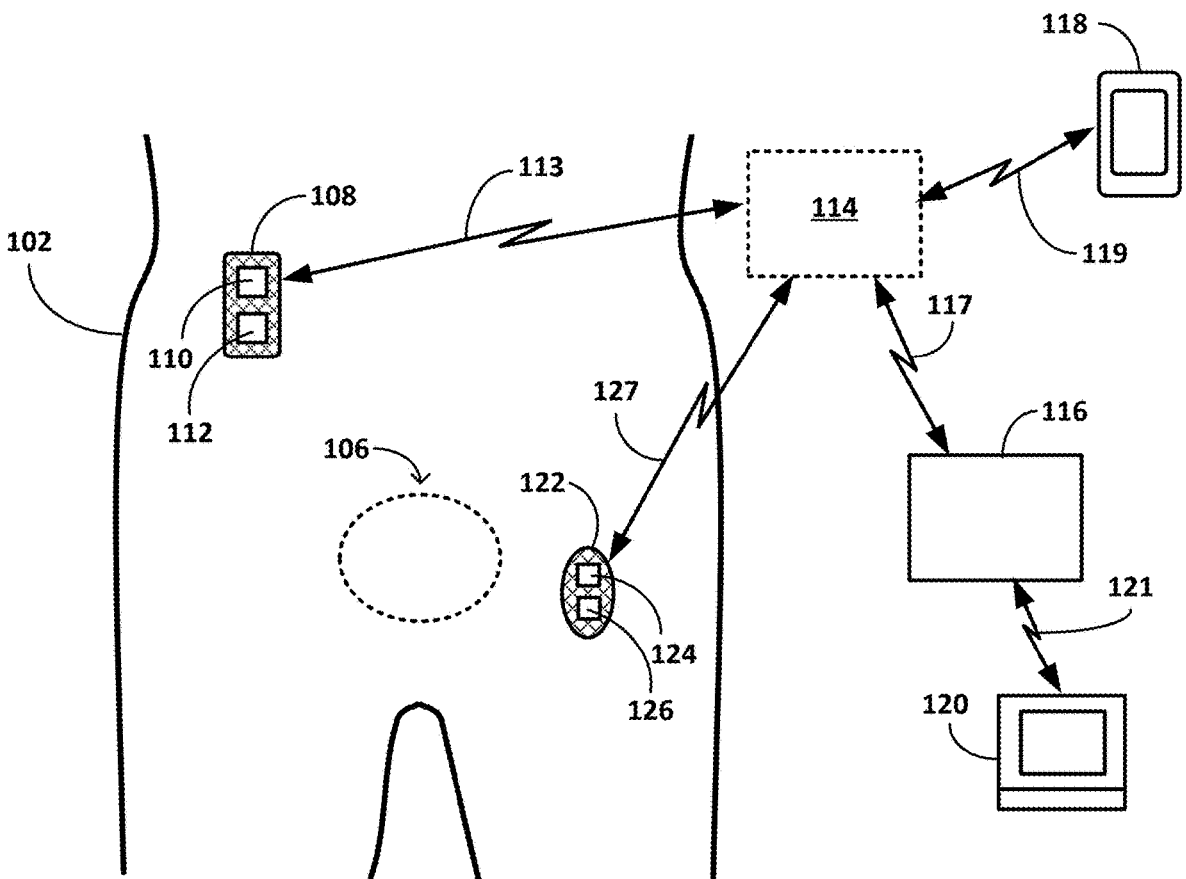
FIG. 1 is a conceptual diagram illustrating an example medical system configured to sense a physiological trait of a patient for an obstetric condition.

In general, the disclosure describes a system configured to sense one or more physiological traits of a patient to monitor and/or assess a likelihood of obstetric conditions in the patient, such as a fertility phase (e.g., menses, a follicular phase, ovulation, a luteal phase), pregnancy, labor, post-partum conditions, and other conditions related to the reproductive system of the patient. The system may use the physiological traits sensed to substantially monitor and track the health of the patient over the course of a conception, a pregnancy, and a post-partum phase when, for example, the patient is outside of a medical clinic setting. The system may provide indications to the patient and/or a clinician when the physiological traits obtained indicate the patient may be ovulating, pregnant, in labor, or experiencing a concerning post-partum condition. The system may thus be configured to assess and indicate reproductive phases for the patient over a life-cycle from the fertility phase to the post-partum phase.

The system may use the physiological traits sensed to monitor and track the health of the patient, as well as indicate when the patient is likely to be experiencing an obstetric condition indicative of a fertility phase, pregnancy, labor, or a post-partum condition. Hence, the system may be used by the patient and/or a clinician as an aid for interpreting when a pregnancy may be relatively likely or relatively unlikely, an aid for tracking the progress of a pregnancy, and/or an aid for indicating a post-partum health of the patient. The system uses the one or more physiological traits sensed from the patient to define one or more patient attributes, such as a hormone level, a muscle contraction, a temperature, a heart rate, a blood pressure level (e.g., systolic and/or diastolic), an oxygen saturation level, a respiration rate, an activity level, a glucose level, a fluid level, and/or other patient attributes. The system is configured to provide communications to the patient and/or a clinician indicating, for example, whether the one or more patient attributes may indicate an obstetric condition of the patient, such as a fertility phase (e.g., menses, a follicular phase, ovulation, a luteal phase), a pregnancy (e.g., indications of a conception and/or a gestational condition during a pregnancy), labor, or a post-partum condition.

In examples, during a pregnancy of the patient, the system is configured to use the sensed physiological traits to monitor and track the health of a fetal patient carried by the patient. As used herein, the one or more physiological traits of the patient may include one or more fetal physiological traits of the fetal patient. A fetal physiological trait may be some measurable phenomena generated by and/or resulting from an anatomical function of the fetal patient carried by the patient. The system may be configured to define one or more fetal attributes using one or more fetal physiological traits. The patient attribute, as used herein, may include one or more fetal attributes, and/or the attribute sign may include a threshold for the one or more fetal attributes. Hence, the system may be configured to monitor patient for obstetric conditions which might impact the patient during a pre-conception or post-partum phase as well as obstetric conditions (e.g., gestational conditions during a pregnancy) which might impact the patient and/or a fetal patient during a pregnancy.

The system is configured to sense the one or more physiological traits using one or more sensors accessible to the patient outside of a medical clinic environment. For example, the one or more sensors may be mechanically supported by a wearable or implantable device. The system may define the one or more patient attributes and communicate information to the patient and/or a clinician, such that the patient and/or the clinician may remain updated without requiring a physical presence of the patient within the medical clinic, and/or without the requiring the patient to laboriously obtain and record the one or more patient attributes (e.g., during a self-evaluation). The system may issue a communication indicative of the one or more patient attributes to a patient input/output device ("patient IO device"), such as a mobile phone, a tablet, or another IO device. The system may issue a communication indicative of the one or more patient attributes to a clinician input/output device ("clinician IO device"), such as a workstation or other IO device. The system may be configured to display the one or more patient attributes or a history of the one or more patient attributes to the patient and/or the clinician, such that the patient and/or clinician may be apprised of the likelihood or unlikelihood of a given obstetric condition for the patient.

Unlike some conventional monitoring and detection systems, the techniques and systems of this disclosure may use a machine learning algorithm to more accurately determine whether one or more sensed physiological traits and/or patient attributes indicate an obstetric condition of the patient. In some examples, the machine learning algorithm is trained with a set of training data comprised of and/or indicative of previously received patient physiological data and/or an assessment input of a clinician. Because the machine learning algorithm is trained with potentially thousands or millions of training instances (e.g., training input vectors), the machine learning algorithm may offer improved performance in the detection of obstetric conditions over a reproductive cycle when compared to conventional monitoring systems and/or techniques. For example, the system may more expeditiously and/or accurately detect indications of a fertility phase, pregnancy, labor, a post-partum phase, and/or other obstetric conditions which might arise over the reproductive cycle.

Additionally, the techniques and systems of this disclosure may be implemented in a medical device such an IMD and/or wearable device that can continuously and/or periodically sense physiological traits of the patient without human intervention and perform millions of operations per second on physiological data to identify obstetric conditions with the machine learning algorithm. Using techniques of this disclosure with a medical device such as an IMD and/or wearable device may be advantageous when a physician cannot be continuously present with the patient over weeks or months to gather and evaluate physiological data and/or where performing millions of operations on weeks or months of physiological data could not practically be performed in the mind of a physician using the techniques of this disclosure (e.g. techniques employing a machine learning algorithm).

The one or more physiological traits (e.g., an electrocardiogram) sensed by the system may be indicative of the one or more patient attributes (e.g., a heart rate). The one or more patient attributes may be indicative of one or more physiological characteristics of the body of the patient (e.g., cardiac activity). In examples, the system compares the one or more patient attributes indicated to an attribute sign indicative of an obstetric condition, such as an obstetric condition indicative of a fertility phase, a pregnancy, labor, or a post-partum condition of the patient. The system may be configured to issue the communication (e.g., to the patient IO device and/or clinician IO device) based on the comparison of the one or more patient attributes indicated with the attribute sign. In some examples, the system is configured to provide recommendations to the patient to take an action in response to the communication. For example, the system might recommend the patient contact a clinician and/or medical facility, go to labor and delivery triage at the hospital, stand and/or walk, and/or make other recommendations. In some examples, the system is configured such that the clinician may input the recommendations to the patient using the clinician IO device, and the system may communicate the recommendations from the clinician IO device to the patient IO device. In some examples, the system may be configured to enable communication between the patient and one or more other individual patients who may be subject to an obstetric condition indicative of a fertility phase, a pregnancy, labor, and/or a post-partum phase to. for example, foster communication between patients and/or enable creation and/or delivery of education materials to the patient and other individual patients.

The system may be configured to define and check the one or more patient attributes on a regular schedule (e.g., twice daily), on a schedule based on an assessed risk, on a substantially continuous basis, when prompted by the patient, clinician, and/or other user, or some combination thereof. For example, the system may increase a frequency at which one or more of the one or more patient attributes are monitored based on an increase in occurrences of a patient attribute exceeding a threshold defined by an attribute sign. The system may decrease a frequency at which one or more patient attributes are monitored based on a decrease in occurrences of a patient attribute falling outside thresholds defined by an attribute sign. In examples, the system is configured to define the patient attribute based on an indicated and/or assessed schedule of the patient. For example, the system may be configured to define the one or more patient attributes when the patient is in a resting condition (based on, e.g., a level of activity movement of the patient, a heart rate of the patient, a schedule provided by the patient, or some other indication). Such scheduling based on a schedule of the patient may improve the indications of the system due to, for example, consistency in the state of the patient (e.g., a resting state, basal state, and/or other state) when the one or more patient attributes are defined). In some examples, the system may be configured to communicate with the patient (e.g., using a patient IO device) to prompt the patient to facilitate sensing of additional physiological traits by the system (e.g., in response to a patient attribute). The system may be configured to prompt the patient to engage one or more additional sensors to facilitate the sensing of the additional physiological traits. For example, the system may communicate with the patient to prompt the patient to engage a percutaneous sensor such as a glucose sensor, a sensor supported by a wearable device, an external sensor such as a weight scale, or some other sensor. The system may be configured to receive sensed outputs from the one or more additional sensors. In examples, the system may be configured to communicate with the patient (e.g., using the patient IO device) when such additional sensing may be discontinued.

The system may be configured to substantially assess the one or more patient attributes to determine if the one or more patient attributes are a normally expected value (e.g., within a normally expected range) or if the one or more patient attributes potentially indicate a condition of concern. The system may assess the one or more patient attributes through comparison with the attribute sign. The attribute sign may describe, for example, a maximum or minimum hormone level for an obstetric condition, a maximum or minimum temperature for an obstetric condition, a maximum or minimum heart rate for an obstetric condition, a maximum or minimum for an obstetric condition, a maximum or minimum oxygen saturation level for an obstetric condition, a maximum or minimum respiration rate for an obstetric condition, a maximum or minimum fluid level (e.g., amniotic fluid, breast milk (e.g., indicative of lactation), etc.) for an obstetric condition, and/or other limits based on a body function of the patient. In examples, a patient attribute and/or attribute sign is based on a plurality and/or combination of the one or more physiological traits sensed (e.g., an ECG and a temperature, or others), such that the system substantially assesses the plurality and/or combination of the one or more physiological traits sensed.

The one or more physiological traits sensed by the system may include any physiological trait sensible by the one or more sensors and influenced by a body function of the patient. For example, the one or more physiological traits may include an electrocardiogram ("ECG"), echocardiogram, electromyography ("EMG"), impedance magnitude, optical signal, a pressure magnitude, an accelerometry reading, an audible sound (e.g., a heart sound), a temperature, and/or any other physiological trait influenced by a body and/or body function of the patient. The patient attribute may be any measure of anatomical function that may be inferred from the one or more physiological traits, such as a hormone level, a body temperature, a fluid level, a heart rate, a blood pressure, an oxygen saturation level (e.g., an SpO2 and/or StO2), a respiration rate, an activity level, or some other anatomical function of the patient. In examples, the system may be configured to define the patient attribute using the one or more physiological traits sensed.

The patient attribute may be based on a combination of substantially different physiological traits indicative of substantially different physiological measures, such as heart rate and blood pressure, respiration rate and muscle contractions, and/or other combinations indicative of substantially different physiological measures. The patient attribute may be substantially based on any singular patient attribute and/or singular physiological trait, and/or may be substantially based on a combination of patient attributes and/or combination of physiological traits indicating a physiological state of the patient. For example, the patient attribute defined may be based substantially on an individual patient attribute, a plurality of patient attributes defined over a time frame, a trend of patient attributes, and/or some other characteristic of one or more patient attributes indicative of an obstetric condition of the patient. The patient attribute defined may be based substantially on an individual physiological trait, a plurality of physiological traits defined over a time frame, a trend of physiological traits, and/or some other characteristic of one or more physiological traits indicative of an obstetric condition of the patient. The patient attribute may be based on a combination of substantially different physiological traits indicative of substantially different physiological characteristics of the patient, such as a combination of an ECG and an optical signal to indicate a hormone level, a combination of an EMG and an accelerometry reading to indicate a uterine contraction, and/or other combinations indicative of substantially different physiological measures to indicate a patient attribute of the patient.

In examples, the system is configured to adjust one or more of the obstetric parameters (e.g., one or more physiologic traits sensed, one or more patient attributes, and/or the one or more attribute signs) utilized based on a particular obstetric condition. For example, the system may assess that the patient is likely in an obstetric condition indicative of a fertility phase (e.g., menses, a follicular phase, ovulation, a luteal phase), pregnancy, labor, or a post-partum condition based on a comparison of the patient attribute and the attribute sign. The system may receive an input (e.g., from the clinician IO device and/or the patient IO device) indicating the patient is likely in an obstetric condition indicative of a fertility phase (e.g., menses, a follicular phase, ovulation, a luteal phase), pregnancy, labor, or a post-partum condition. The system may be configured to adjust the obstetric parameters sensed and/or utilized based on the assessment and/or input. For example, the system may be configured to use one or more sets of first obstetric parameters to assess whether the patient is ovulating. The system may be configured to use one or more second obstetric parameters once ovulation is assessed or otherwise indicated to detect, for example, a possible pregnancy. The system may be configured to use one or more third obstetric parameters once pregnancy is assessed or otherwise indicated to, for example, monitor the health of the patient and/or a fetal patient during the pregnancy. The system may be configured to use one or more fourth obstetric parameters once labor is assessed or otherwise indicated to, for example, monitor the health of the patient and/or a fetal patient during labor. The system may be configured to use one or more fifth obstetric parameters once a post-partum phase is assessed or otherwise indicated to, for example, monitor the patient for one or more post-partum conditions. Likewise, the system may be configured to adjust a schedule by which the obstetric parameters are obtained and/or assessed based on a particular obstetric condition. The system may be configured to direct the one or more sensors to sense the one or more physiological traits based on the obstetric condition. In examples, the system is configured to communicate with the patient (e.g., using a patient IO device) and/or a clinician (e.g., using a clinician IO device) when the system adjusts one or more of the obstetric parameters and/or assesses and obstetric condition. Hence, the system may be configured to assess and indicate reproductive phases for the patient over a life-cycle from the fertility phase to the post-partum phase.

In addition to issuing the communication based on the patient attribute and the attribute sign, the system may be configured to record and/or store the periodically sensed one or more physiological traits and patient attributes to enable a clinician and/or the patient to review a history over some portion of or substantially all of a time interval. The system may be configured to record and/or store the periodically sensed one or more physiological traits and patient attributes to provide the history. In examples, the system is configured to communicate the sensed one or more physiological traits and/or patient attributes on a scheduled basis (e.g., twice daily), such that the history remains substantially updated. The system may communicate the sensed one or more physiological traits and/or patient attributes to the external device to indicate the history to a clinician using the clinician IO device. The system may communicate the sensed one or more physiological traits and/or patient attributes to the patient IO device to indicate the history to the patient or another user. In some examples, the system is configured to communicate a first set of the one or more sensed physiological traits and/or patient attributes to the external device for review by a clinician and communicate a second set of the one or more sensed physiological traits and/or patient attributes to the patient IO device for review by the patient or other user. The first set communicated to the clinician IO device may be different from or substantially similar to the second set communicated to the patient IO device.

The system includes one or more sensors configured to sense the one or more physiological traits. The system may include sensing circuitry operably connected to the one or more sensors. The sensing circuitry may be configured to communicate one or more output signals indicative of the one or more physiological traits sensed to processing circuitry operably connected to the sensing circuitry. The processing circuitry may be configured to cause the one or more sensors and/or the sensing circuitry to communicate (e.g., periodically communicate) the one or more output signals. The processing circuitry may be configured to receive (e.g., periodically receive) the one or more output signals and define one or more patient attributes using the one or more output signals. In examples, the system includes a medical device mechanically supporting one or more of the sensors. The medical device may be, for example, an implantable medical device ("IMD") or other medical device configured to remain with and/or accessible to the patient when the patient is in an ambulatory state (e.g., outside of a clinic setting). The medical device may mechanically support at least some portion of the sensing circuitry and/or the processing circuitry. In some examples, the medical device mechanically supports a first portion of the processing circuitry and/or sensing circuitry, and an external device separate from (e.g., displaced from) the medical device mechanically supports a second portion of the processing circuitry. The medical device may include communications circuitry configured to cause the first portion of the processing circuitry to communicate with the second portion of the processing circuitry to, for example, issue a communication indicative of an assessment of a patient attribute, record and/or store the periodically sensed physiological traits and/or patient attributes, and/or for other reasons.

In examples, the system is configured to sense a plurality of physiological traits using the one of more sensors. The system may be configured to define a plurality of patient attributes using the plurality of physiological traits. The attribute sign may be dependent on one or more of the plurality of patient attributes. For example, an attribute sign may be dependent on a single patient attribute (e.g., a body temperature indicative of, for example, ovulation, a fluid level indicative of lactation), and the system may issue the communication based on comparison of the single patient attribute defined and the singly-dependent attribute sign. An attribute sign may be dependent on a combination of patient attributes defined (e.g., patient heart rate and uterine muscle contractions indicative of, for example, false labor), and the system may issue the communication based on a comparison of the combination of multiple patient attributes defined and the multiply-dependent attribute sign. Hence, the system may be configured to monitor for the obstetric condition using one or more patient attributes sensed from the patient.

The system (e.g., the processing circuitry) may be configured to define and/or refine the attribute sign to reduce a rate of false positives when comparing the one or more patient attributes to the attribute sign. For example, the system may be configured to utilize the periodically sensed one or more physiological traits, patient parameters indicative of the one or more physiological traits, and/or patient attributes (also termed "patient physiological data") to define and/or refine the attribute sign. In examples, the system (e.g., the processing circuitry) implements a machine learning algorithm trained with a training data set based on the patient physiological data. The machine learning algorithm may be configured to define and/or refine the attribute sign using the patient physiological data, such that the system may be substantially personalized to the patient.

In examples, the system is configured to receive an assessment input from a user input device (e.g., the patient IO device and/or the clinician IO device) indicative of an assessment of whether the system issued an appropriate communication (e.g., an appropriately tiered communication) when a set of patient physiological data was previously received. The training data set of the machine learning algorithm may be based on the previously received patient physiological data and/or the assessment input, such that the communications may be substantially tailored to the one or more physiological traits of the individual patient. The substantial tailoring to the individual patient may reduce a rate of false positives indicating necessary action communicated by the system.

In some examples, the system (e.g., the processing circuitry) may be configured to define and/or refine the attribute sign based on population data sensed from a population of other individual patients potentially subject to one or more of the obstetric conditions. The system (e.g., the processing circuitry) may include a machine learning algorithm configured to define and/or refine the attribute sign using the population data. In examples, the machine learning algorithm is trained using a training data set including the population data. The population data may include, for example, individual physiological traits sensed from the individual patients, individual patient parameters based on the individual physiological traits, and/or individual patient attributes defined for the individual patients. In examples, an external device of the system may be configured to communicate with a plurality of individual medical devices worn, implanted within, and/or otherwise utilized by the population of other individual patients. The medical system may communicate with the plurality of individual medical devices to gather the population data.

In examples, the medical system may be implemented using one or more computer programs implemented on programmable computers, such as computers that include, for example, processing capabilities, data storage (e.g., volatile or nonvolatile memory and/or storage elements), input devices, and output devices. Program code and/or logic described herein may be applied to input data to perform the functionality described herein and generate desired output information. The programs may be stored on any suitable device, e.g., a storage media, readable by a general or special purpose program running on a computer system (e.g., including processing apparatus) and configuring the computer system to perform functions described herein. Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g., a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1 is a conceptual diagram illustrating an example medical system 100 configured to sense one or more physiological traits of a patient 102 to monitor for obstetric conditions in the patient, such as a fertility phase (e.g., menses, a follicular phase, ovulation, a luteal phase), pregnancy, labor, post-partum conditions, and other conditions related to the reproduction system 106 of patient 102. The reproduction system 106 of patient 102 includes, for example, a uterus, ovaries, fallopian tubes, and/or other organs and anatomical structures associated with reproduction. System 100 includes one or more medical devices such as medical device 108. Medical device 108 may mechanically support and/or otherwise be operably connected to sensor 110 and sensing circuitry 112. System 100 includes processing circuitry 114. In examples, system 100 includes an external device 116. Processing circuitry 114 may be mechanically supported by medical device 108 or external device 116. In examples, medical device 108 mechanically supports a first portion of processing circuitry 114 and external device 116 mechanically supports a second portion of processing circuitry 114. System 100 may include patient IO device 118 and/or clinician IO device 120.

In examples, medical system 100 is configured to determine and/or alter the obstetric parameters of patient 102 (e.g., a physiologic trait, the patient attribute, and/or the attribute sign) obtained and evaluated utilized based on an particular obstetric condition of patient 102. For example, the system may assess and/or receive an indication (e.g., from patient 102 and/or a clinician) that the patient is likely in an obstetric condition indicative of a fertility phase, pregnancy, labor, or a post-partum condition based on a comparison of one or more patient attributes and one or more attribute signs. The system may be configured to adjust the obstetric parameters sensed and/or utilized based on the assessment and/or input. For example, the system may be configured to use a one or more first obstetric parameters to monitor patient 102 for ovulation, one or more second obstetric parameters once ovulation is indicated, one or more third obstetric parameters once pregnancy is indicated, one or more fourth obstetric parameters once labor is indicated, and/or one or more fifth obstetric parameters once a post-partum phase is indicated. Likewise, medical system 100 may be configured to determine and/or alter the obstetric parameters based on an individual phase of an obstetric condition, such as an individual trimester of a pregnancy of another phase of an obstetric condition. Hence, the system may be configured to assess and indicate reproductive phases for the patient over a life-cycle from a fertility phase (e.g., menses, a follicular phase, ovulation, a luteal phase) to a post-partum phase.

Figure 2:
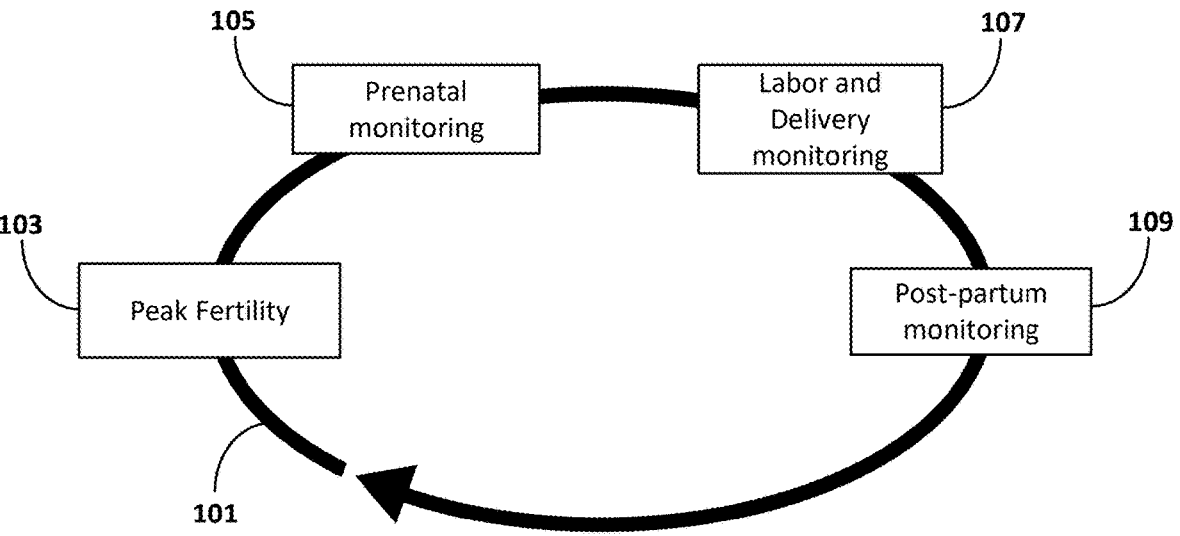
FIG. 2 is a conceptual diagram illustrating one or more phases over which the medical system of FIG. 1 may sense the physiological trait.

Medical system 100 may be configured to monitor patient 102 for obstetric conditions which might occur over a reproductive lifecycle 101 of patient 102, such as illustrated in FIG. 2. Medical system 100 may be configured to provide monitoring for the obstetric conditions during various phases (e.g., some or all phases) which might occur over the reproductive lifecycle of patient 102. For example, medical system 100 may be configured to provide fertility monitoring (e.g., peak fertility) of patient 102 over some or all of a fertility phase 103 (menses, a follicular phase, ovulation, a luteal phase), provide prenatal monitoring over some or all of a pregnancy 105 (e.g., monitor for a conception and/or a gestational condition during a pregnancy), provide labor and delivery monitoring over some or all of a labor 107, and/or provide post-partum monitoring over some or all of a post-partum phase 109. Medical system may be configured to monitor patient 102 during time periods between one or more of fertility phase 103, pregnancy 105, labor 107, and/or post-partum phase 109. For example, medical system 100 may be configured to monitor patient 102 over a reproductive cycle which includes substantially all phases (e.g., fertility phase 103, pregnancy 105, labor 107, post-partum phase 109), or over a portion of a reproductive cycle which includes less than all phases (e.g., including fertility phase 103, but not one or more of pregnancy 105, labor 107, and/or post-partum phase 109).

Hence, medical system 100 may be configured to monitor patient 102 for obstetric conditions over substantially all or some portion of reproductive lifecycle 101. Medical system 100 may be configured to monitor patient 102 over time periods exceeding a typical extent of reproductive cycle 101 and/or between occurrences of some portion or all of reproductive cycle 101, such that medical system 100 may monitor patient 102 during at least a portion of the child-bearing years of patient 102. For example, medical system 100 may be configured to provide monitoring of patient 102 over multiple reproductive lifecycles, such as a first reproductive lifecycle including a first pregnancy and second reproductive lifecycle including a second pregnancy. Further, although reproductive cycle 101 is illustrated at FIG. 2 as proceeding from a first phase (e.g., fertility phase 102) to a second phase (e.g., pregnancy 105) for illustrative clarity, medical system 100 may be configured to monitor patient 102 over the first phase (e.g., one of fertility phase 103, pregnancy 105, labor 107, or post-partum phase 109) without proceeding to a second phase (e.g., another of fertility phase 103, pregnancy 105, labor 107, or post-partum phase 109) until the physiological traits of patient 102 indicate such a subsequent phase may be occurring.

For example, medical system 100 may be configured to substantially monitor patient 102 for an obstetric condition associated with fertility phase 103 (e.g., a high or low likelihood of pregnancy) until the physiological traits of patient 102 indicate patient 102 may have entered a subsequent phase of reproduction cycle 101 (e.g., pregnancy 105). Medical system 100 may be configured to substantially monitor patient 102 for an obstetric condition associated with pregnancy phase 105 until labor 107 is indicated. Medical system 100 may be configured to substantially monitor patient 102 for an obstetric condition associated with labor 107 until post-partum phase 109 is indicated. Further, although reproductive cycle 101 is illustrated at FIG. 2 as including distinct and separate phases for illustrative clarity, medical system 100 may be configured to monitor and assess a likelihood of any potential obstetric condition of patient 102 regardless of a particular phase in reproductive lifecycle 101 that patient 102 may be assessed as experiencing.

Medical system 100 may be configured to provide an indication to patient 102 that patient 102 may be experiencing a fertility phase 103, a pregnancy 105, labor 107, or a post-partum phase 109. Medical system 100 may thus be configured to assess and/or provide an indication that patient 102 may be more or less likely to conceive based on the physiological traits sensed, whether patient 102 may have experienced or be experiencing one of more prenatal conditions of concern, and/or whether patient 102 may have experienced or be experiencing one of more post-partum conditions of concern. In examples, medical system 100 may be configured to monitor patient 102 over time periods when a fertility phase 103, a pregnancy 105, labor 107, or a post-partum phase 109 is not occurring, such that medical system 100 may apprise patient 102 of when an obstetric condition is likely or unlikely to occur during a particular time period and/or particular point in time. In examples, medical system 100 is configured for use over one or more of life-cycles 101. Hence, the system may be configured to assess and indicate reproductive phases for patient 102 over a life-cycle from fertility phase 103 to post-partum phase 109, as well as assess and indicate to patient 102 whether that one or more of the obstetric conditions may be likely or unlikely.

Figure 3:
FIG. 3 is a conceptual diagram illustrating the example medical system of FIG. 1 configured to sense a physiological trait of a patient carrying a fetal patient.
Figure 3:
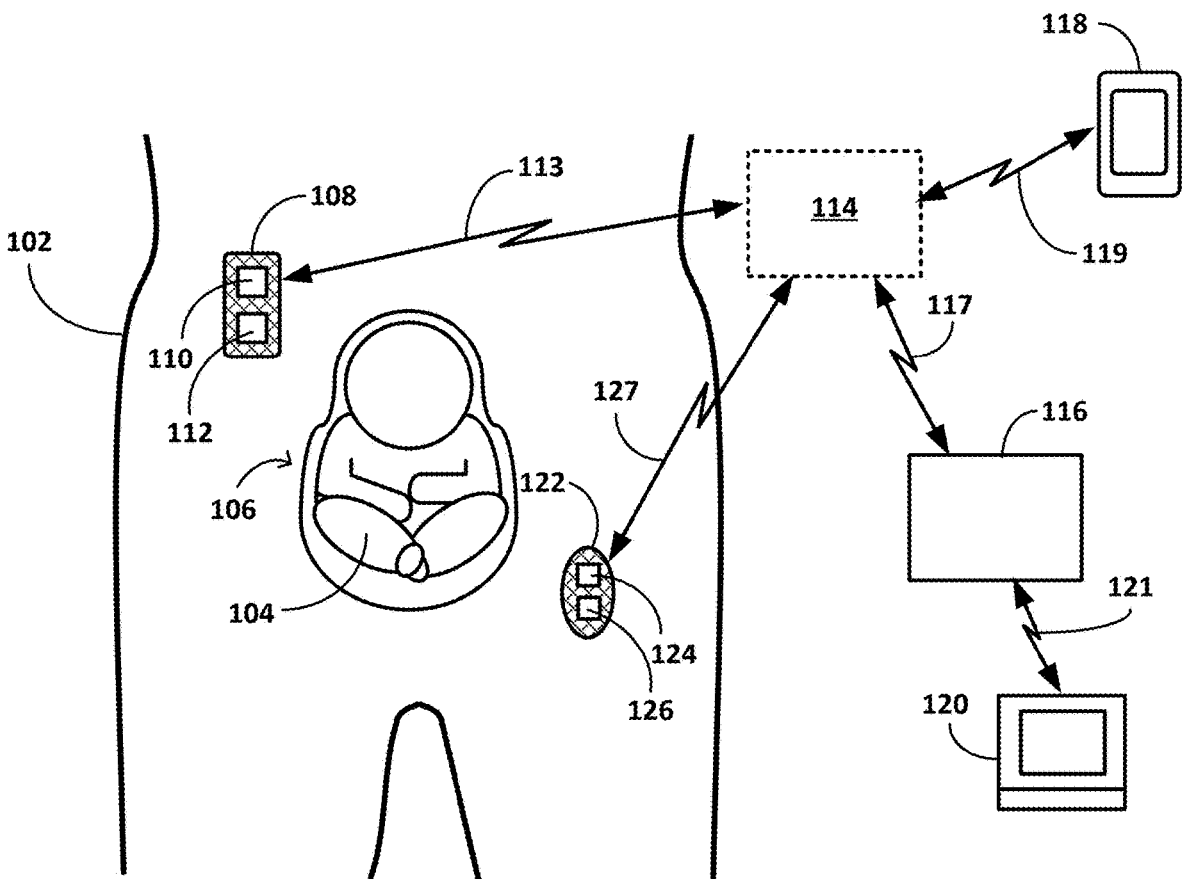

FIG. 3 is a conceptual diagram illustrating medical system 100 configured to sense one or more physiological traits of patient 102 carrying a fetal patient 104 in reproduction system 106 (e.g., within a uterus). As used herein, the one or more physiological traits of patient 102 may include one or more fetal physiological traits of fetal patient 104. A fetal physiological trait may be some measurable phenomena generated by and/or resulting from an anatomical function of fetal patient 104 carried by patient 102. System 100 may be configured to define one or more fetal attributes using the one or more fetal physiological traits indicated by and/or inferred from the one or more physiological traits of patient 102. A fetal attribute may be, for example, a heart rate of fetal patient 104, a blood pressure of fetal patient 104, an oxygen saturation level of fetal patient 104, a respiration rate of fetal patient 104, a body temperature of fetal patient 104, an activity level of fetal patient 104, or some other anatomical function of fetal patient 104. The patient attribute may include one or more of the fetal attributes of fetal patient 104. The attribute sign may include a threshold for the one or more fetal attributes of fetal patient 104. Hence medical system 100 may be configured to monitor patient 102 for obstetric conditions which might impact patient 102 during a pre-conception or post-partum phase as well as obstetric conditions which might impact patient 102 and/or fetal patient 104 during a pregnancy. Hence, system 100 may be configured to monitor patient 102 and/or fetal patient 104 for gestational conditions which might arise during a pregnancy.

Medical system 100 is configured to obtain and evaluate one or more of the obstetric parameters (e.g., one or more of the patient limit, the physiologic traits sensed, the patient attribute, and/or the attribute sign) utilized based on an particular obstetric condition. For example, the system may assess that the patient is likely in an obstetric condition indicative of a fertility phase, pregnancy, labor, or a post-partum condition based on a comparison of the patient attribute and the attribute sign. The system may receive an input (e.g., from the clinician IO device and/or the patient IO device) indicating the patient is likely in an obstetric condition indicative of a fertility phase, pregnancy, labor, or a post-partum condition. The system may be configured to adjust the obstetric parameters sensed and/or utilized based on the assessment and/or input. For example, the system may be configured to use one or more sets of first obstetric parameters to assess whether the patient is ovulating. The system may be configured to use one or more second obstetric parameters once ovulation is assessed or otherwise indicated to detect, for example, a possible pregnancy. The system may be configured to use one or more third obstetric parameters once pregnancy is assessed or otherwise indicated to, for example, monitor the health of the patient and/or a fetal patient during the pregnancy. The system may be configured to use one or more fourth obstetric parameters once labor is assessed or otherwise indicated to, for example, monitor the health of the patient and/or a fetal patient during labor. The system may be configured to use one or more fifth obstetric parameters once a post-partum phase is assessed or otherwise indicated to, for example, monitor the patient for one or more post-partum conditions. Likewise, the system may be configured to adjust a schedule by which the obstetric parameters are obtained and/or assessed based on an particular obstetric condition. Hence, the system may be configured to assess and indicate reproductive phases for the patient over a life-cycle from the fertility phase to the post-partum phase.

Sensor 110 is configured to sense one or more physiological traits of patient 102. A physiological trait may be some measurable phenomena generated by the body of patient 102 and indicative of one or more patient attributes of patient 102. For example, the physiological trait may be an electrocardiogram ("ECG"), echocardiogram, electromyography, impedance magnitude, optical signal, a body temperature, a pressure magnitude, an accelerometry reading, an audible sound, and/or any other physiological trait influenced by a body of patient and fetus 102. Sensing circuitry 112 is configured to provide one or more output signals indicative of the one or more physiological traits to processing circuitry 114.

Processing circuitry 114 is configured to define one or more patient attributes of patient 102 using the one or more output signals. A patient attribute may be any measure of anatomical function that may be inferred from the one or more physiological traits, such as a hormone level of patient 102, a body temperature of patient 102, a heart rate of patient 102, a blood pressure of patient 102, an oxygen saturation level of patient 102, a respiration rate of patient 102, a fluid level of patient 102, an activity level of patient 102, or some other anatomical function of patient 102. In some examples, a patient attribute may be substantially based on a single physiological trait (e.g., a heart rate based on an ECG, a body temperature based on a temperature measurement, and/or other patient attributes based substantially on a single physiological trait). In some examples, a patient attribute may be based on a plurality of physiological traits (e.g., a hormone level based on two or more of an ECG, an oxygen saturation, an optical signal, and/or another physiological trait, a uterine contraction based on two or more of an electromyography, an accelerometry reading and/or another physiological trait, and/or other patient attributes based substantially on two or more physiological traits).

In examples, medical device 108 is configured to position relative to patient 102 such that sensor 110 may sense the physiological trait. Medical device 108 may be, for example, an implantable device configured to implant within patient 102 to position sensor 110. Medical device 108 may be a device configured to substantially non-invasively contact a body of patient 102 to position sensor 110 (e.g., smartwatch and/or other smart apparel). Medical device 108 may be a device configured to position sensor 110 through a manipulation by and/or action of patient 102 (e.g., a weight scale, a blood pressure cuff, a urine sampling device, and/or a glucose testing device). Although described primarily in the context of examples in which medical device 108 takes the form of a device configured to be implanted within patient 102, the techniques of this disclosure may be implemented in systems including any one or more implantable or external devices configured to position sensor 110 such that sensor 110 may to sense a physiological trait of patient 102. In some examples, medical device 108 may be an insertable cardiac monitor or loop recorder, such as that disclosed in U.S. patent application Ser. No. 15/081,216, incorporated herein by reference in its entirety.

Sensing circuitry 112 is configured to communicate (e.g., via link 113) one or more output signals to processing circuitry 114 indicative of the physiological trait sensed by sensor 110. Processing circuitry 114 is configured to define the patient attribute of patient 102 using the one or more output signals. For example, processing circuitry 114 may be configured to define a patient attribute such as a hormone level, a temperature, a heart rate, a systolic blood pressure, a diastolic blood pressure, an oxygen saturation (e.g., an SpO2 indicative of blood oxygen saturation and/or an StO2 indicative of tissue oxygen saturation), a respiration rate, a fluid level (e.g., amniotic fluid, breastmilk, or other fluid), a blood glucose level, a body weight, a muscle contraction, an activity level, and/or other patient attribute of patient 102 using the one or more output signals. Processing circuitry 114 is configured to issue a communication to patient IO device 118, external device 116, and/or clinician IO device 120 indicative of the patient attribute, such that the patient 102 and/or the clinician may remain apprised of the likelihood or unlikelihood of a given obstetric condition for patient 102.

In examples, processing circuitry 114 is configured to communicate at least some portion of the patient physiological data sensed and/or defined (e.g., the physiological trait, a patient parameter indicative of the physiological trait, and/or the patient attribute) to patient IO device 118, external device 116, and/or clinician IO device 120. In some examples, processing circuitry 114 is configured to communicate a first portion of the patient physiological data to patient IO device 118 and a second portion of the patient physiological data to external device 116 such that, for example, patient IO device 118 displays information useful to patient 102 while external device 116 causes the display of additional and/or different information which might be useful to a clinician.

In examples, patient IO device 118, external device 116, and/or clinician IO device 120 may take the form of personal computing devices of patient 102 and/or a clinician, such as a smartphone, smartwatch, or other smart apparel of patient 102 or the clinician. Patient IO device 118, external device 116, and/or clinician IO device 120 may be any computing device configured for wireless communication with processing circuitry 114, such as a desktop, laptop, or tablet computer, a smart home controller, alarm, thermostat, speaker, or other smart appliance, or any Internet of Things (IoT) device. Patient IO device 118, external device 116, and/or clinician IO device 120 may be configured to communicate with processing circuitry 114 and each other according to the Bluetooth® or Bluetooth® Low Energy (BLE and/or BTLE) protocols, as examples. In some examples, the processing circuitry 114 may be configured to enable communication between patient IO device 118 and one or more other individual patient IO devices (e.g., patient IO devices of individual patients 148, 150, 156). This may foster communication between patient 102 and individual patients 148, 150, 156 to, for example, enable and/or assist in the creation and/or delivery of education materials to patient 102 and/or individual patients 148. 150, 156.

Processing circuitry 114 is configured to compare the patient attribute to an attribute sign to substantially monitor patient 102. The attribute sign may define, for example, a maximum or minimum hormone level, a maximum or minimum body temperature, a maximum or minimum heart rate, a maximum or minimum systolic blood pressure, a maximum or minimum diastolic blood pressure, a maximum or minimum oxygen saturation level, a maximum or minimum respiration rate, a maximum or minimum body weight, a maximum or minimum blood glucose level, a maximum or minimum activity level, a maximum or minimum amniotic fluid level, and/or some other defined attribute sign. Processing circuitry 114 may be configured to issue the communication to patient IO device 118 (e.g., via link 119), external device 116 (e.g., via link 117), and/or clinician IO device 120 (e.g., via link 121 or another communication link) based on the comparison. Processing circuitry 114 may be configured to cause patient IO device 118, external device 116, and/or clinician IO device 120 to provide an output sensible (e.g., able to be sensed) by the prenatal patient, a clinician, or another user when processing circuitry 114 issues the communication. For example, the sensible output may include a visual output, audio output, haptic output, or some other output which may be sensed by one or more of the senses of a human being.

In examples, processing circuitry 114 may be configured to issue the communication using a tiered communication indicative of an assessment of the comparison. The tiered communication system may provide for earlier and/or more accurate notifications to the maternal patient and/or a clinician regarding the likelihood or unlikelihood of a given obstetric condition for the patient. The tiered communication system may provide an indication that a fertility phase, pregnancy, labor, and/or a post-partum condition is unlikely, somewhat likely, and/or very likely to have occurred or be occurring based on the comparison of a patient attribute and an attribute sign. For example, when patient 102 is assessed as pregnant, the tiered communication system may serve as an indication that preeclampsia, gestational diabetes, and/or conditions potentially placing the patient 102 and/or a carried fetal patient at risk may have occurred or could potentially occur.

Processing circuitry 114 may be configured to define a tier of a communication based on a plurality of attribute signs (e.g., a first attribute sign, a second attribute sign, and/or a third attribute sign) defined for patient 102. For example, processing circuitry 114 may be configured to issue a Tier I communication when the patient attribute is assessed to be a normally expected value (e.g., within a range defined by the first attribute sign). Processing circuitry 114 may be configured to issue a Tier II communication when the patient attribute is assessed to potentially indicate a condition warranting further evaluation and/or action by patient 102 and/or a clinician (e.g., within a range defined by the second attribute sign.) Processing circuitry 114 may be configured to issue a Tier III communication when the patient attribute is assessed to indicate a condition potentially more serious and/or warranting more urgent action and/or action by patient 102 and/or a clinician (e.g., within a range defined by the third attribute sign). The tiered communication system may define any number of tiers and any number of attribute signs. In some examples, processing circuitry 114 may be configured to cause patient IO device 118 and/or clinician IO device 120 to provide visible, audible, or other indicia associated with a tier of the communication. For example, processing circuitry 114 may be configured to cause patient IO device 118 and/or clinician IO device 120 to provide a first indicia (e.g., a green background) for a Tier I communication, a second indicia (e.g., a yellow background) for a Tier II communication, and/or a third indicia (e.g., a red background) for a Tier III communication.

In addition to or instead of issuing the communications, processing circuitry 114 may be configured to record and/or store the patient physiological data periodically sensed to enable a clinician and/or patient 102 to review a history over some portion of or substantially the entirety of a time interval. For example, processing circuitry 114 may be configured to communicate the patient physiological data from medical device 108 to external device 116, clinician IO device 120, and/or patient IO device 118. Processing circuitry 114 may be configured to communicate the patient physiological data on a scheduled basis (e.g., twice daily, or on some other schedule), such that the history remains substantially updated. In examples, processing circuitry 114 is configured to alter the operation of medical system 100 based on an input received from clinician IO device 120, based on one or more tiered communications, and/or for other reasons. For example, processing circuitry 114 may cause medical system 100 to increase or decrease a frequency at which sensor 110 senses a particular patient physical trait based on a received input from clinician IO device 120, based on one or more tiered communications, and/or for other reasons. Processing circuitry 114 may cause medical system 100 to alter and/or adjust the one or more physiological traits sensed by medical device 108 based on a received input from clinician IO device 120, based on one or more tiered communications, and/or for other reasons. Processing circuitry 114 may cause medical system 100 to alter and/or adjust the scheduled basis by which processing circuitry 114 provides the patient physiological data to external device 116 based on a received input from clinician IO device 120, based on one or more tiered communications, and/or for other reasons. Processing circuitry 114 may cause medical system 100 to alter and/or adjust one or more attribute signs used by processing circuitry 114 based on a received input from clinician IO device 120, based on one or more tiered communications, and/or for other reasons. In examples, processing circuitry 114 is configured to communicate with patient IO device 118 and/or a clinician IO device 120 when the processing circuitry 114 adjusts and/or alters the patient physiological data sensed, and/or assesses that one or more obstetric conditions indicative of a fertility phase, a pregnancy, labor, and/or a post-partum condition has been or may be experienced by patient 102.

In some examples, medical system 100 includes a plurality of sensors. The plurality of sensors may be configured to sense a physiological trait of patient 102. For example, medical system 100 may include a second medical device 122 including a sensor 124 and/or sensing circuitry 126. Sensing circuitry 126 may be configured to communicate (e.g., via link 127) one or more output signals to processing circuitry 114 indicative of a physiological trait sensed by sensor 124. For example, medical device 108 may be configured to primarily sense a first physiological trait using sensor 110 and a second physiological trait using sensor 124. Medical system 100 may be configured to define a first patient attribute using the first physiological trait and define a second patient attribute using the second physiological trait. In some examples, processing circuitry may be configured to define the patient attribute using either or both of the first physiological trait and the second physiological trait. Second medical device 122 may mechanically support at least some portion of processing circuitry 114. Second medical device 122, sensor 124, and/or sensing circuitry 126 may be configured similar to medical device 108, sensor 124, and/or sensing circuitry 112 respectively. In some examples, second medical device 122 (e.g., a housing of medical device 122) is configured to contact the body of patient 102 at an anatomical location different from the location of medical device 108 (e.g., a housing of medical device 108) to, for example, more effectively sense the first physiological trait and/or the second physiological trait, and/or for some other reason. In examples, processing circuitry 114 may be configured to communicate with patient 102 (e.g., using patient IO device 118) to prompt patient 102 to facilitate sensing of additional physiological traits. Processing circuitry 114 may be configured to prompt patient 102 to engage one or more additional sensors to facilitate the sensing of the additional physiological traits. For example, processing circuitry 114 may be configured to prompt the patient to engage a percutaneous sensor such as a glucose sensor, a sensor supported by a wearable device, an external sensor such as a weight scale, or some other sensor. Processing circuitry 114 may be configured to receive sensed outputs from the one or more additional sensors. In examples, the processing circuitry 114 may be configured to communicate with patient 102 (e.g., using patient IO device 118) when the additional physiological traits have been sufficiently sensed (e.g., such that the additional sensing may be discontinued). In some examples, medical device 122 may be an insertable cardiac monitor or loop recorder, such as that disclosed in U.S. patent application Ser. No. 15/081,216, incorporated herein by reference in its entirety.

In some examples, medical system 100 (e.g., one or more of an electrode, an optical sensor, an accelerometer, a sound sensor, a temperature sensor, pressure sensor, and/or another of sensor 110, 124) is configured to sense a signal indicative of a hormone level within patient 102. Processing circuitry 114 may be configured to define a patient attribute indicative of a hormone level of patient 102 using the one or more output signals provided by sensing circuitry 112, 126. For examples, processing circuitry 114 may be configured to define the patient attribute indicative of a hormone level using one or more sensors including a sensor configured to detect a physiological trait indicative of a heart rate of patient 102 (e.g., an ECG). Processing circuitry 114 may be configured to define the patient attribute indicative of a hormone level using, for example, a heart rate variability and/or other parameters defined using the heart rate. Processing circuitry 114 may define the patient attribute indicative of a hormone level using additional sensors and/or output signals, such as a urine sampling device, a weight scale, a blood pressure cuff, a temperature sensor, and/or other sensors and/or output signals indicative of a hormone level of patient 102. In examples, the patient attribute indicative of the hormone level (and/or any patient attribute) may be based on a plurality of signals indicative of the hormone level received over a period of time (e.g., a statistical parameter, a trend, or other attributes based on the plurality). Processing circuitry 114 may compare the patient attribute to an attribute sign indicative of a maximum hormone level of patient 102 for an obstetric condition, a minimum hormone level of patient 102 for an obstetric condition, and/or another attribute sign defined using the hormone level singly or in combination with other physiological traits. In some examples, processing circuitry 114 may use the hormone level sensed (e.g., as indicated by the one or more output signals) to define a patient attribute combining the hormone level and another physiological trait sensed by medical system 100. Processing circuitry 114 may issue a communication to patient IO device 118, external device 116, and/or clinician IO device 120 based on the comparison of the patient attribute and the attribute sign.

For example, processing circuitry 114 may compare a hormone level of patient 102 to a maximum hormone level for Luteinizing hormone, Follicle-stimulating hormone, Human chorionic gonadotropin hormone, estrogen, progesterone, or a maximum hormone level for another hormone indicative of an obstetric condition. Processing circuitry 114 may compare a hormone level of patient 102 to a minimum hormone level for Luteinizing hormone, Follicle-stimulating hormone, Human chorionic gonadotropin hormone, estrogen, progesterone, or a minimum hormone level for another hormone indicative of an obstetric condition. Processing circuitry 114 may issue a tiered communication based on the maximum hormone level, the minimum hormone level, another attribute sign, and/or determined deviations therefrom.

In examples, processing circuitry 114 is configured to monitor patient 102 for an obstetric condition associated with one or more of a fertility phase, pregnancy, labor, and/or a post-partum phase using the patient attribute indicative of a hormone level. The patient attribute may be defined using the signal indicative of the hormone level singly or in combination with other patient attributes and/or physiological characteristics, such as a body temperature (e.g., basal body temperature), a weight measure (e.g., a body mass index (BMI)), a blood sample, and/or others. In examples, processing circuitry 114 is configured to assess than patient 102 is likely to be experiencing ovulation based on a patient attribute defined using a hormone level of Luteinizing hormone. Processing circuitry 114 may be configured to assess that patient 102 may have a high likelihood of pregnancy (e.g., peak fertility) based on the assessment of ovulation. For example, processing circuitry 114 may be configured to assess a high likelihood of pregnancy based on a period of time (e.g., 1 or more days) since ovulation was assessed.

Processing circuitry 114 may be configured to communicate an indication of peak fertility to patient 102 (e.g., using patient IO device 118). In examples, processing circuitry 114 may be configured to estimate a time period when ovulation might be expected for patient 102 using the patient attribute indicative of a hormone level (e.g., based on a trend of the patient attribute), and use the estimated ovulation time period to inform patient 102 (e.g., using patient IO device 118) when a peak fertility period is likely to occur (e.g., inform patient 102 prior to an assessment of ovulation by patient 102). In some examples, processing circuitry may be configured to assess a risk of miscarriage using the patient attribute indicative of a hormone level. For example, Processing circuitry 114 may be configured to determine a patient attribute defined using a hormone level of progesterone (PdG) singly or in combination with other patient attributes and/or physiological characteristics to assess the risk of miscarriage. (e.g., based on a low PdG level).

In some examples, medical system 100 (e.g., an electrode of sensor 110, 124) is configured to sense a signal indicative of an ECG of patient 102. Processing circuitry 114 may be configured to define a patient attribute (e.g., a heart rate and/or another patient attribute defined using the ECG) of patient 102 using the one or more output signals provided by sensing circuitry 112, 126. Processing circuitry 114 may compare the patient attribute to an attribute sign indicative of, for example, a maximum heart rate of patient 102 for an obstetric condition, a minimum heart rate of patient 102 for an obstetric condition, and/or another attribute sign defined using one or more output signals indicative of the ECG singly or in combination with other physiological traits. In some examples, processing circuitry 114 may use the ECG sensed (e.g., as indicated by the one or more output signals) to define a patient attribute combining the ECG sensed and another physiological trait sensed by medical system 100. Processing circuitry 114 may issue a communication to patient IO device 118, external device 116, and/or clinician IO device 120 based on the comparison of the patient attribute and the attribute sign.

For example, processing circuitry 114 may compare the heart rate of patient 102 to a maximum heart rate (e.g., 100 beats/minute (bpm) or another maximum heart rate) for an obstetric condition and/or a minimum heart rate (e.g., 60 bpm or another minimum heart rate) for an obstetric condition. Processing circuitry 114 may issue a tiered communication based on the maximum heart rate, the minimum heart rate, another attribute sign, and/or determined deviations therefrom.

In some examples, medical system 100 (e.g., an optical sensor of sensor 110, 124) is configured to sense a signal indicative of a blood pressure of patient 102. Processing circuitry 114 may be configured to define a patient attribute indicative of a systolic pressure and/or diastolic pressure of patient 102 using the one or more output signals provided by sensing circuitry 112, 126. Processing circuitry 114 may compare the patient attribute to an attribute sign indicative of, for example, a maximum systolic pressure of patient 102 for an obstetric condition, a minimum systolic pressure of patient 102 for an obstetric condition, a maximum diastolic pressure of patient 102 for an obstetric condition, a minimum diastolic pressure of patient 102 for an obstetric condition, and/or another attribute sign defined using the blood pressure singly or in combination with other physiological traits. In some examples, processing circuitry 114 may use the blood pressure sensed (e.g., as indicated by the one or more output signals) to define a patient attribute combining the blood pressure sensed and another physiological trait sensed by medical system 100. In examples, the patient attribute indicative of the blood pressure (and/or any patient attribute) may be based on a plurality of signals indicative of the blood pressure received over a period of time (e.g., a statistical parameter, a trend, or other attributes based on the plurality). Processing circuitry 114 may issue a communication to patient IO device 118, external device 116, and/or clinician IO device 120 based on the comparison of the patient attribute and the attribute sign.

For example, processing circuitry 114 may compare the systolic pressure of patient 102 to a maximum systolic pressure (e.g., 130 mmHg or another maximum systolic pressure) for an obstetric condition and/or a minimum systolic pressure (e.g., 100 mmHg or another minimum systolic pressure) for an obstetric condition. Processing circuitry 114 may compare the diastolic pressure of patient 102 to a maximum diastolic pressure (e.g., 80 mmHg or another maximum diastolic pressure) for an obstetric condition and/or a minimum diastolic pressure (e.g., 60 mmHg or another minimum diastolic pressure) for an obstetric condition. Processing circuitry 114 may issue a tiered communication based on the maximum systolic pressure, minimum systolic pressure, maximum diastolic pressure, minimum diastolic pressure, another attribute sign, and/or determined deviations therefrom.

In some examples, medical system 100 (e.g., an optical sensor of sensor 110, 124) is configured to sense a signal indicative of an oxygen saturation of patient 102. Processing circuitry 114 may be configured to define a patient attribute indicative of an oxygen saturation level of patient 102 using the one or more output signals provided by sensing circuitry 112, 126. Processing circuitry 114 may compare the patient attribute to an attribute sign indicative of a maximum oxygen saturation level of patient 102 for an obstetric condition, a minimum oxygen saturation level of patient 102 for an obstetric condition, and/or another attribute sign defined using the oxygen saturation singly or in combination with other physiological traits. In some examples, processing circuitry 114 may use the oxygen saturation level sensed (e.g., as indicated by the one or more output signals) to define a patient attribute combining the oxygen saturation level and another physiological trait sensed by medical system 100. Processing circuitry 114 may issue a communication to patient IO device 118, external device 116, and/or clinician IO device 120 based on the comparison of the patient attribute and the attribute sign.

For example, processing circuitry 114 may compare the oxygen saturation of patient 102 to a maximum oxygen saturation (e.g., 100%) for an obstetric condition and/or a minimum oxygen saturation (e.g., 95%) for an obstetric condition. Processing circuitry 114 may issue a tiered communication based on the maximum oxygen saturation, the minimum oxygen saturation, and/or determined deviations therefrom.

In some examples, medical system 100 (e.g., an accelerometer and/or an electrode of sensor 110, 124) is configured to sense a signal indicative of a respiration of patient 102. Processing circuitry 114 may be configured to define a patient attribute indicative of a respiration rate of patient 102 using the one or more output signals provided by sensing circuitry 112, 126. Processing circuitry 114 may compare the patient attribute to an attribute sign indicative of a maximum respiration rate of patient 102 for an obstetric condition, a minimum respiration rate of patient 102 for an obstetric condition, and/or another attribute sign defined using the respiration rate singly or in combination with other physiological traits. In some examples, processing circuitry 114 may use the respiration rate sensed (e.g., as indicated by the one or more output signals) to define a patient attribute combining the respiration rate and another physiological trait sensed by medical system 100. Processing circuitry 114 may issue a communication to patient IO device 118, external device 116, and/or clinician IO device 120 based on the comparison of the patient attribute and the attribute sign.

For example, processing circuitry 114 may compare the respiration rate of patient 102 to a maximum respiration rate (e.g., 16 breaths per minute (bpm)) and/or a minimum respiration rate (e.g., 12 bpm). Processing circuitry 114 may compare the respiration rate of fetal patient 104 to a maximum respiration rate (e.g., 70 bpm) and/or a minimum respiration rate (e.g., 30 bpm). Processing circuitry 114 may issue a tiered communication based on the maximum respiration rate, the minimum respiration rate, and/or determined deviations therefrom.

In some examples, medical system 100 (e.g., a resistive network and/or an optical sensor of sensor 110, 124) is configured to sense a signal indicative of a temperature of patient 102. Processing circuitry 114 may be configured to define a patient attribute indicative of a body temperature of patient 102 using the one or more output signals provided by sensing circuitry 112, 126. Processing circuitry 114 may compare the patient attribute to an attribute sign indicative of a maximum body temperature of patient 102 for an obstetric condition, a minimum body temperature of patient 102 for an obstetric condition, and/or another attribute sign defined using the body temperature singly or in combination with other physiological traits. In some examples, processing circuitry 114 may use the body temperature sensed (e.g., as indicated by the one or more output signals) to define a patient attribute combining the body temperature and another physiological trait sensed by medical system 100. Processing circuitry 114 may issue a communication to patient IO device 118, external device 116, and/or clinician IO device 120 based on the comparison of the patient attribute and the attribute sign.

For example, processing circuitry 114 may compare the temperature of patient 102 to a maximum temperature (e.g., 99.3 degrees F.) and/or a minimum temperature (e.g., 97.9 degrees F.). Processing circuitry 114 may compare the temperature of fetal patient 104 (e.g., a temperature of patient 102+1 degree F.) to a maximum temperature and/or a minimum temperature. Processing circuitry 114 may issue a tiered communication based on the maximum temperature, the minimum temperature, and/or determined deviations therefrom.

In examples, processing circuitry 114 is configured to monitor patient 102 for an obstetric condition associated with one or more of a fertility phase, pregnancy, labor, and/or a post-partum phase using the patient attribute indicative of a body temperature (e.g., a basal body temperature) of patient 102. For example, processing circuitry 114 may be configured to assess than patient 102 is likely to be experiencing ovulation based on a patient attribute defined using the body temperature of patient 102. The patient attribute may be defined using the signal indicative of the temperature singly or in combination with other patient attributes and/or physiological characteristics, such as a weight measure (e.g., a body mass index (BMI)), a fluid level (e.g., a level of cervical mucus), and/or others. For example, processing circuitry 114 may be configured to assess a body temperature of patient 102 during a time period (e.g., over a menstrual cycle, over a fertility phase, or substantially over a reproductive cycle) to establish a temperature history of patient 102. Processing circuitry 114 may be configured to assess patient 102 as potentially ovulating based on an increase in body temperature above that expected based on the temperature history. In examples, processing circuitry 114 is configured to sense the body temperature when patient 102 is in a resting state (e.g., based on sensed motion of patient 102 or other indicators), such that the body temperature is representative of a basal body temperature. Processing circuitry 114 may be configured to assess that patient 102 may have a high likelihood of pregnancy (e.g., peak fertility) based on the assessment of ovulation.

In some examples, medical system 100 (e.g., an electrode of sensor 110, 124) is configured to sense a signal indicative of an electromyography signal of patient 102, an electrohysterography signal of patient 102, or another signal indicative of a muscle contraction (e.g., a uterine muscle contraction) of patient 102. Processing circuitry 114 may be configured to define a patient attribute indicative of a muscle contraction of patient 102 using the one or more output signals provided by sensing circuitry 112, 126. Processing circuitry 114 may compare the patient attribute to an attribute sign indicative of a maximum muscle contraction of patient 102 for an obstetric condition, a minimum muscle contraction of patient 102 for an obstetric condition, and/or another attribute sign defined using the muscle contraction singly or in combination with other physiological traits. In some examples, processing circuitry 114 may use the muscle contraction sensed (e.g., as indicated by the one or more output signals) to define a patient attribute combining the muscle contraction and another physiological trait sensed by medical system 100. Processing circuitry 114 may issue a communication to patient IO device 118, external device 116, and/or clinician IO device 120 based on the comparison of the patient attribute and the attribute sign.

In examples, processing circuitry 114 is configured to monitor patient 102 for an obstetric condition associated with one or more of a fertility phase, pregnancy, labor, and/or a post-partum phase using the patient attribute indicative of a muscle contraction (e.g., a uterine muscle contraction) of patient 102. The patient attribute indicative of the muscle contraction may be defined using the signal indicative of the muscle contraction singly or in combination with other patient attributes and/or physiological characteristics, such as a heart rate, a blood pressure, and/or others. In examples, the patient attribute is indicative of a repetition of the sensed muscle contraction (e.g., a pattern of muscle contractions versus time). Processing circuitry 114 may compare the patient attribute to an attribute sign indicative of a maternal labor experienced by patient 102 or a false labor experienced by patient 102. Processing circuitry 114 may issue a communication to patient IO device 118, external device 116, and/or clinician IO device 120 based on the comparison of the patient attribute and the attribute sign.

In some examples, medical system 100 (e.g., a glucose sensor of sensor 110, 124, and/or an electrode (e.g., an electrooxidizing anode) of sensor 110, 124) is configured to sense a glucose signal of patient 102, a signal indicative of a glucose level of patient 102 (e.g., an ECG), or another signal indicative of a glucose level of patient 102 (e.g., an optical signal). Processing circuitry 114 may be configured to define a patient attribute indicative of a glucose level of patient 102 using the one or more output signals provided by sensing circuitry 112, 126. Processing circuitry 114 may compare the patient attribute to an attribute sign indicative of a maximum glucose level of patient 102 for an obstetric condition, a minimum glucose level of patient 102 for an obstetric condition, and/or another attribute sign defined using the glucose level singly or in combination with other physiological traits. In some examples, processing circuitry 114 may use the glucose level sensed (e.g., as indicated by the one or more output signals) to define a patient attribute combining the glucose level and another physiological trait sensed by medical system 100. For example, processing circuitry 114 may compare the patient attribute to an attribute sign indicative of a maximum glucose level potentially indicating gestational diabetes when patient 102 is carrying fetal patient 104. In examples, the patient attribute indicative of the glucose level (and/or any patient attribute) may be based on a plurality of signals indicative of the glucose level received over a period of time (e.g., a statistical parameter, a trend, or other attributes based on the plurality). Processing circuitry 114 may issue a communication to patient IO device 118, external device 116, and/or clinician IO device 120 based on the comparison of the patient attribute and the attribute sign.

In some examples, medical system 100 (e.g., an electrode of sensor 110, 124) is configured to sense an impedance or another signal indicative of a fluid (e.g., amniotic fluid, breast milk (e.g., indicative of lactation), cervical mucus (e.g., indicative of ovulation)) in patient 102. Processing circuitry 114 may be configured to define a patient attribute indicative of a fluid level of patient 102 using the one or more output signals provided by sensing circuitry 112, 126. Processing circuitry 114 may compare the patient attribute to an attribute sign indicative of a maximum fluid level of patient 102 for an obstetric condition, a minimum fluid level of patient 102 for an obstetric condition, and/or another attribute sign defined using the fluid level singly or in combination with other physiological traits. In some examples, processing circuitry 114 may use the fluid level sensed (e.g., as indicated by the one or more output signals) to define a patient attribute combining the fluid level and another physiological trait sensed by medical system 100. Processing circuitry 114 may issue a communication to patient IO device 118, external device 116, and/or clinician IO device 120 based on the comparison of the patient attribute and the attribute sign.

In addition to the examples above, processing circuitry 114 may use at least a first physiological trait sensed and a second physiological trait sensed to define a patient attribute combining at least the first physiological trait and the second physiological trait. The first physiological trait may be, for example, one of an ECG, echocardiogram, electromyography, impedance magnitude, optical signal, a pressure magnitude, an accelerometry reading, an audible sound, a temperature, and/or any other physiological trait influenced by a body function of patient 102. The second physiological trait may be, for example, another of an ECG, echocardiogram, electromyography, impedance magnitude, optical signal, a pressure magnitude, an accelerometry reading, an audible sound, a temperature, and/or any other physiological trait influenced by a body function of patient 102. Processing circuitry 114 may compare the patient attribute defined using the combined first physiological trait and the second physiological trait sensed to an attribute sign defining a threshold for the combined first physiological trait and the second physiological trait. Processing circuitry 114 may issue a communication to patient IO device 118, external device 116, and/or clinician IO device 120 based on the comparison of the patient attribute and the attribute sign.

In some examples, processing circuitry 114 may use at least a first patient attribute sensed and a second patient attribute sensed to define a patient attribute combining at least the first patient attribute and the second patient attribute. The first patient attribute may be, for example, one of a hormone level, a muscle contraction, a body temperature, a heart rate, a blood pressure level, an oxygen saturation level, a respiration rate, an activity level, a glucose level, a fluid level, and/or another patient attribute defined using a physiological trait of patient 102. The second patient attribute may be, for example, another of a hormone level, a muscle contraction, a body temperature, a heart rate, a blood pressure level, an oxygen saturation level, a respiration rate, an activity level, a glucose level, a fluid level, and/or another patient attribute defined using a physiological trait of patient 102. Processing circuitry 114 may compare the patient attribute defined using the combined first patient attribute and the second patient attribute to an attribute sign defining a threshold for the combined first patient attribute and the second patient attribute. Processing circuitry 114 may issue a communication to patient IO device 118, external device 116, and/or clinician IO device 120 based on the comparison of the patient attribute and the attribute sign.

Figure 4:
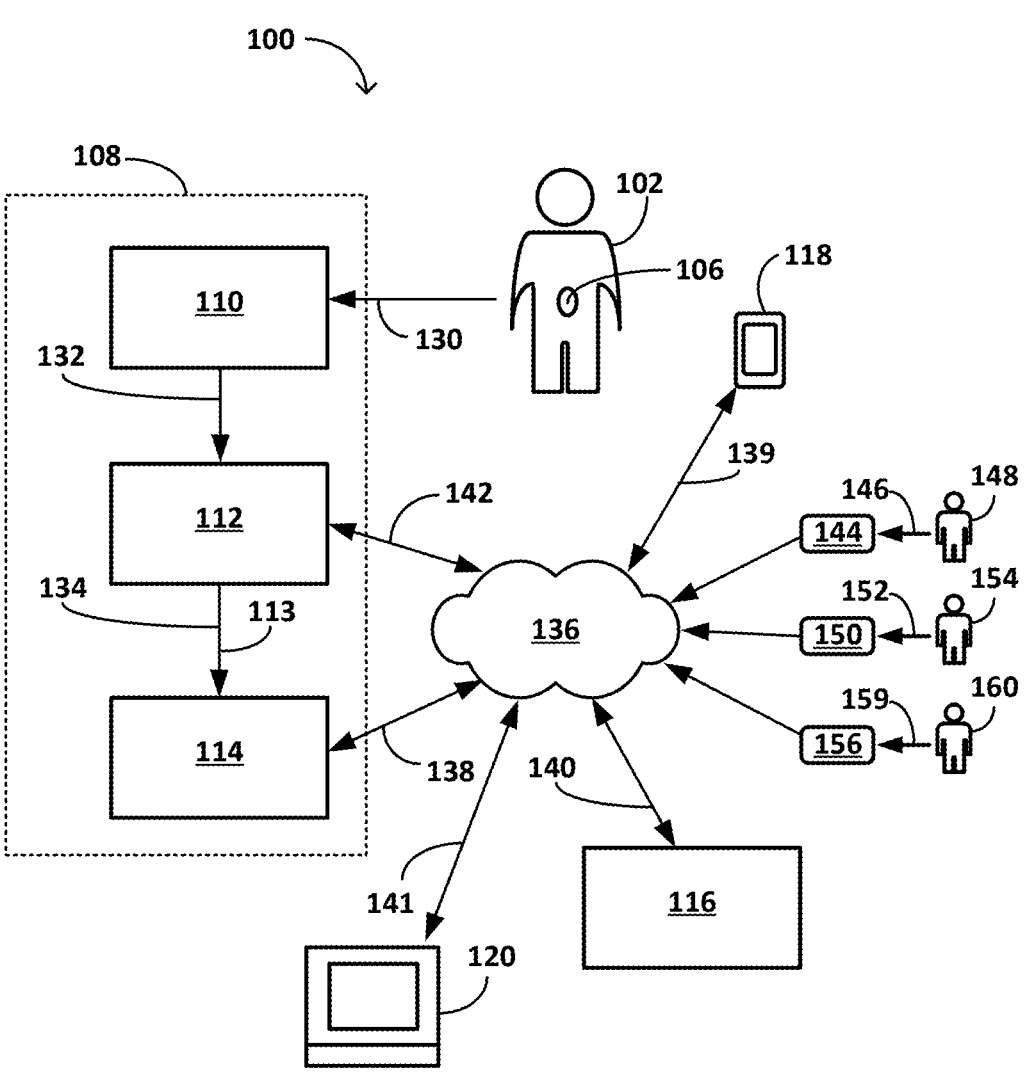
FIG. 4 is a block diagram illustrating example communications of the medical system of FIG. 1.

FIG. 4 illustrates a block diagram of an example technique conducted by medical system 100 to monitor one or more physiological traits of patient 102. As discussed, the one or more physiological traits of patient 102 may include one or more physiological traits of fetal patient 104 (FIG. 3). Sensor 110 may sense input information 130 generated by the body of patient 102 and provide output information 132 to sensing circuitry 112. The input information may be indicative of the one or more physiological traits of patient 102, such as a cardiac activity, systolic and/or diastolic blood pressure, oxygen saturation, respiration rate, a body temperature, muscular activity, emitted light, audible sound, a weight, a glucose level, or other physiological trait from which a patient attribute may be inferred. As discussed, the patient attribute may include one or more fetal attributes. Sensing circuitry 112 may be configured to convert the output information 132 into one or more output signals 134 ("output signals 134") usable by processing circuitry 114, such as a digital electrical signal, an analog electrical signal, an optical signal, and/or or some other signal. Processing circuitry 114 is configured to receive output signals 134 (e.g., via link 113 (FIG. 1)) and define the patient attribute using output signals 134. Processing circuitry is configured to issue a communication to patient IO device 118, external device 116, and/or clinician IO device 120 based on a comparison of the patient attribute with a attribute sign and/or a comparison of the fetal attribute with a fetal limit.

Processing circuitry 114 may be configured to communicate with patient IO device 118, external device 116, and/or clinician IO device 120 via a network 136. For example, similar to the use of link 119 (FIG. 1), processing circuitry 114 may be configured to communicate with patient IO device 118 via network 136 using link 138 and link 139. Similar to the use of link 117 (FIG. 1), processing circuitry 114 may be configured to communicate with external device 116 via network 136 using link 138 and link 140. Processing circuitry 114 may be configured to communicate with clinician IO device 120 via network 136 using link 138 and link 141. In examples, similar to the use of link 121 (FIG. 1), external device 116 is configured to communicate with clinician IO device 120 via network 136 using link 140 and link 141. In some examples, sensing circuitry 112 is configured to communicate with processing circuitry 114 (e.g., to communicate output signals 134) via network 136 using link 142 and link 138.

Processing circuitry 114 may transmit data (e.g., patient physiological data) received from sensing circuitry 112 to patient IO device 118, external device 116, and/or clinician IO device 120 via network 136. Clinician IO device 120, external device 116, and or patient IO device 118 may comprise computing devices configured to allow users, e.g., clinicians treating patient 102 and other patients, to interact with data collected from sensing circuitry 112. In some examples, sensor 110, sensing circuitry 112, processing circuitry 114, clinician IO device 120, external device 116, and/or patient IO device 118 include one or more handheld computing devices, computer workstations, servers, or other networked computing devices. In some examples, sensor 110, sensing circuitry 112, and/or at least some portion of processing circuitry 114 is mechanically supported by medical device 108.

Network 136 may include one or more computing devices (not shown), such as one or more non-edge switches, routers, hubs, gateways, security devices such as firewalls, intrusion detection, and/or intrusion prevention devices, servers, cellular base stations and nodes, wireless access points, bridges, cable modems, application accelerators, or other network devices. Network 136 may include one or more networks administered by service providers, and may thus form part of a large-scale public network infrastructure, e.g., the Internet. Network 136 may provide circuitry and/or devices, such as processing circuitry 114, sensing circuitry 112, external device 116, clinician IO device 120, and/or patient IO device 118, access to the Internet, and may provide a communication framework that allows processing circuitry 114, sensing circuitry 112, external device 116, clinician IO device 120, and/or patient IO device 118 to communicate with one another. In some examples, network 136 may include a private network that provides a communication framework that allows processing circuitry 114, sensing circuitry 112, external device 116, clinician IO device 120, and/or patient IO device 118 to communicate with each other, but isolates one or more of these devices or data flows between these device from devices external to the private network for security purposes. In some examples, the communications between processing circuitry 114, sensing circuitry 112, external device 116, clinician IO device 120, and/or patient IO device 118 are encrypted.

Medical device 108 may mechanically support at least some portion of processing circuitry 114. In some examples, medical device 108 mechanically supports a first portion of processing circuitry 114, and external device 116, clinician IO device 120, patient IO device 118, and/or network 136 mechanically supports a second portion of processing circuitry 114. Processing circuitry 114 may include any circuitry and/or devices of external device 116, clinician IO device 120, patient IO device 118, and/or network 136 to perform the techniques described herein. In examples, processing circuitry 114 is configured to utilize population data sensed from a population of individual patients potentially subject to one or more of the obstetric conditions. In examples, external device 116 and/or network 136 is configured to communicate with a plurality of individual medical devices worn, implanted within, and/or otherwise utilized by the population of individual patients to gather the population data. For example, external device 116 and/or network 136 may be configured to communicate with individual medical device 144 (e.g., via link 146) to sense one or more physiological traits from an individual patient 148, communicate with individual medical device 150 (e.g., via link 152) to sense one or more physiological traits from an individual patient 154, and/or communicate with individual medical device 156 (e.g., via link 159) to sense one or more physiological traits from an individual patient 160.

Sensor 110 may include any devices, circuitry, structures, reagents, or other materials configured such that sensor 110 may sense input information 130 indicative of one or more physiological traits of patient 102. The one or more physiological traits of patient 102 may include one or more fetal physiological traits of fetal patient 104. For example, sensor 110 may include an electrode configured to sense an electric potential, an impedance, a current, and/or some other electrical phenomena influenced by (e.g., generated by and/or transmitted through) a body of patient 102 (e.g., to sense an ECG signal, an electromyography signal, a temperature, a glucose level, and/or some other physiological trait). Sensor 110 may include a sound transducer configured to sense a sound wave influenced by (e.g., generated by, reflected by, and/or transmitted through) a body of patient 102 (e.g., to sense an echocardiogram signal, a generated sound, and/or some other physiological trait). Sensor 110 may include a light transmitter and/or receiver configured to transmit light to and/or sense light emitted from (e.g., reflected by) a body of patient 102 (e.g., to sense a blood pressure, an oxygen saturation, and/or some other physiological trait). Sensor 110 may include an accelerometer configured to sense a motion generated by a body of patient 102 and/or a body of fetal patient 104 (e.g., to sense a patient activity level, a fetal activity level, a respiration, and/or some other physiological trait). Sensor 110 may include a force transducer configured to sense a force imparted from a body of patient 102 and/or fetal patient 104 (e.g., to sense a patient weight, a blood pressure, and/or some other physiological trait).

Sensing circuitry 112 is configured to receive the output information 132 from sensor 110 and issue output signals 134 to processing circuitry 114. In examples, sensing circuitry 112 may be configured to define and/or refine the output information using a machine learning algorithm trained using population data indicative of output signals sensed from patient 102 and/or a population of other individual patients potentially subject to one or more of the obstetric conditions (e.g., patient 148, patient 154, and/or patient 160). In some examples, sensor 110 includes a first sensor configured to sense a first physiological trait of patient 102 and a second sensor configured to sense a second physiological trait of patient 102. In some examples, the first physiological trait or the second physiological trait includes a fetal physiological trait of fetal patient 104. Output signals 134 may include a first output signal indicative of the first physiological trait and a second output signal indicative of the fetal physiological trait. In some examples, sensor 110 is configured to sense a mixed physiological trait indicative of both a physiological trait of patient 102 and a fetal physiological trait of fetal patient 104, and output signals 134 is a mixed output signal indicative of both the physiological trait and the fetal physiological trait.

Processing circuitry 114 may be configured to define any patient attribute indicative of a physiological characteristic of patient 102 using output signal 134. In examples, processing circuitry 114 is configured to define one or more patient attributes including one or more of a hormone level of patient 102, a body temperature of patient 102, a heart rate of patient 102, a systolic pressure of patient 102, a diastolic pressure of patient 102, an oxygen saturation level of patient 102, a respiration rate of patient 102, and/or other patient attributes. As discussed, the one or more patient attributes may include one or more fetal attributes including one or more of a heart rate of fetal patient 104, a systolic pressure of fetal patient 104, a diastolic pressure of fetal patient 104, an oxygen saturation level of fetal patient 104, a respiration rate of fetal patient 104, a temperature of fetal patient 104, and/or other fetal attributes. Processing circuitry 114 is configured to compare the patient attribute to an attribute sign to substantially monitor patient 102 for an obstetric condition. The attribute sign may define any threshold for a patient attribute, including a maximum of minimum hormone level, a maximum or minimum heart rate, a maximum or minimum systolic blood pressure, a maximum or minimum diastolic blood pressure, a maximum or minimum oxygen saturation level, a maximum or minimum respiration rate, a maximum or minimum body temperature, a maximum or minimum fluid level, a maximum or minimum body weight, a maximum or minimum blood glucose level, a maximum or minimum activity level, or some other defined attribute sign.

In examples, processing circuitry 114 is configured to receive a mixed output signal indicative of both the first physiological trait of patient 102 and the second physiological trait of patient 102. Processing circuitry may define a first patient attribute and a second patient attribute using the mixed output signal. Processing circuitry 114 and/or sensing circuitry 112 may be configured to preprocess the mixed output signal (e.g., using linear filtering or another preprocessing technique) to enhance a patient signal source indicative of the first patient attribute and/or the second patient attribute. In examples, processing circuitry 114 is configured to use a machine learning algorithm to, for example, improve an accuracy of and/or reduce input requirements of the patient signal source. In examples, processing circuitry 114 is configured to use at least a first mixed output signal and a second mixed output signal to define the patient attribute. The first mixed output signal and the second mixed output signal may be indicative of the patient signal source. For example, the first mixed output signal may be indicative of a mixed physiological trait sensed using a first sensing element (e.g., a first electrode) of sensor 110 or sensor 124 (FIG. 1). The second mixed output signal may be indicative of a mixed physiological trait sensed using a second sensing element (e.g., a second electrode) of sensor 110 or sensor 124 (FIG. 1). In examples, a first medical device (e.g., medical device 108) provides the first mixed output signal and a second medical device (e.g., medical device 122) provides the second mixed output signal.

In some examples, processing circuitry 114 is configured to perform some portion of or substantially all of the signal separation technique to define the first patient attribute and/or the second patient attribute. In some examples, processing circuitry 114 is configured to communicate data indicative of the mixed output signal to circuitry of another device (e.g., external device 116, network 136, patient IO device 118, and/or clinician device 120) and receive a communication indicative of the first patient attribute and/or second from the other device. Processing circuitry 114 may be configured to define the first patient attribute and/or the second patient attribute using the communication indicative of the first patient attribute and/or second patient attribute received from the other device.

Processing circuitry 114 may be configured to define and/or refine the attribute sign to, for example, reduce a rate of false positives when comparing the patient attribute to the attribute sign. In examples, processing circuitry 114 is configured to utilize a model developed by a machine learning algorithm trained with a training data set based on the patient physiological data sensed using sensor 110 to define and/or refine the attribute sign. In examples, processing circuitry 114 is configured to receive an assessment input from a user input device (e.g., clinician IO device 120) indicative of an assessment of whether processing circuitry 114 issued an appropriate communication (e.g., an appropriately tiered communication) when a previously received set of patient physiological data ("prior patient data") was communicated. Processing circuitry 114 may be configured to train the machine learning algorithm using the prior patient data and/or the assessment input provided, such that the attribute sign may be substantially personalized to patient 102. In examples, rather than or in addition to being provided from a user input device, the assessment input may be accessed by processing circuitry 114 via one or more of medical device 108, second medical device 122, external device 116, patient input/output device 118, network 136, or another portion of system 100

In examples, processing circuitry 114 is configured to formulate one or more training data sets using the assessment input (e.g., from clinician IO device 120) and the prior patient data. A training data set formulated may include a plurality of training input vectors representative of the prior patient data and a plurality of training output vectors representative of the assessment input received for the prior patient data, with each training input vector associated with a corresponding training output vector. Processing circuitry 114 may formulate a given input vector by defining one or more elements of the given input vector, where the one or more elements are indicative of some portion of the prior patient data. Processing circuitry 114 may formulate an associated training output vector by defining one or more elements of the associated training output vector, where the one or more elements of the training output vector are indicative of the assessment input received. The assessment input received may indicate, for example, whether a training input vector described or is likely to describe one or more obstetric condition for the patient.

Processing circuitry 114 may group each training input vector and associated training output vector in a data pair, such that processing circuitry 114 formulates a plurality of data pairs. Processing circuitry 114 may define a training data set using the plurality of data pairs and, in some examples, train the machine learning algorithm using the training data set. Once trained with the training data set, the machine learning algorithm may be trained to receive a current input vector indicative of patient physiological data and map the current input vector onto an output space defined at least in part by the plurality of training output vectors. Processing circuitry 114 may define and/or refine the attribute sign based on the output space defined. In examples, processing circuitry 114 is configured to compare the patient attribute to the attribute sign based on the mapping of the current input vector onto the output space defined. In some examples, the attribute sign defines a vector within the output space.

In examples, processing circuitry 114 may be configured to define and/or refine the attribute sign using a machine learning algorithm trained using population data sensed from a population of other individual patients potentially subject to one or more of the obstetric conditions (e.g., patient 148, patient 154, and/or patient 160). The machine learning algorithm may be trained using the population data. For example, machine learning algorithm may be trained using a population training data set including a plurality of population input vectors representative of the population data and a plurality of population output vectors indicative of an associated evaluation input. A population input vector may describe, for example, physiological data received for an individual patient within the population. An evaluation input may indicate, for example, whether a population input vector described one or more obstetric conditions for the individual prenatal patient. Each population input vector may be associated with a population output vector. Once trained with the population training data set, the machine learning algorithm may be trained to receive a current input vector indicative of patient physiological data and map the current input vector onto a population output space defined at least in part by the plurality of population output vectors. Processing circuitry 114 may define and/or refine the attribute sign based on the population output space defined. In examples, processing circuitry 114 is configured to compare the patient attribute to the attribute sign based on the mapping of the current input vector onto the population output space defined. In some examples, the patient attribute defines a vector within the population output space.

In examples, processing circuitry 114 is configured to gather the population data from the population of other individual patients potentially subject to one or more of the obstetric conditions (e.g., patient 148, patient 154, and/or patient 160). For example, processing circuitry 114 may be configured to communicate with individual medical device 144 to collect one or more physiological traits from individual patient 148, communicate with individual medical device 150 to collect one or more physiological traits from individual patient 154, and/or communicate with individual medical device 156 to collect one or more physiological traits from individual patient 160. Processing circuitry 114 may be configured to formulate the population training data set using the population data gathered. In examples, processing circuitry is configured to train the machine learning algorithm using the population training data set.

Processing circuitry 114 (and/or sensing circuitry 112) may include one or more processing circuits configured to implement the machine learning algorithm, such as a neural network, a deep learning system, or another type of machine learning system. In examples, processing circuitry 114 is configured to implement the machine learning algorithm using one or more neural network systems, deep learning systems, or other types of supervised or unsupervised machine learning systems. For example, the machine learning algorithm may be implemented by a feedforward neural network, such as a convolutional neural network, a radial basis function neural network, a recurrent neural network, a modular or associative neural network. Examples of machine learning algorithms that may be so configured to perform aspects of this disclosure include can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, Convolution Neural Networks (CNN), Long Short Term Networks (LSTM), the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In examples, a neural network utilized by processing circuitry 114 includes a plurality of artificial neurons. The artificial neurons may be present within one or more layers of the neural network. For example, the artificial neurons may present within an input layer of the neural network, an output layer of the neural network, and one or more hidden layers between the input layer and the output layer. The input layer may include one or more input artificial neurons. The output layer may include one or more output artificial neurons. The artificial neurons may be configured to receive a signal at an input of the artificial neuron and process the signal at an output of the artificial neuron (e.g., process the signal using a parameter of the artificial neuron). The artificial neuron may include a plurality of inputs and a plurality of outputs. The artificial neuron may be configured to receive the input from the output of a separate artificial neuron, and may be configured to pass the processed signal from its output to the input of another artificial neuron. The processing of the signal conducted by the artificial neuron may be adjusted by the artificial neuron as training of the machine learning algorithm proceeds. Processing circuitry 114 may be configured to train the machine learning algorithm using the training data set and/or population training data set in any manner causing the machine learning algorithm to converge as the training proceeds. In examples, processing circuitry 114 is configured to use a first portion of the training data set and/or population training data set to cause the machine learning algorithm to converge and a second portion of the training data set and/or population training data set to validation test and/or blind test the training conducted with the first portion.

As discussed, any of external device 116, clinician IO device 120. Patient IO device 118, network 136, and/or medical devices 108, 122, 144, 150, 156 may include, mechanically support, and/or house some portion of or substantially all of processing circuitry 114. Any of external device 116, clinician IO device 120. Patient IO device 118, network 136, and/or medical devices 108, 122, 144, 150, 156 may perform any of the functionality ascribed to processing circuitry 114. Likewise, any of external device 116, clinician IO device 120. Patient IO device 118, network 136, and/or medical devices 108, 122, 144, 150, 156 may perform any of the functionality ascribed to any other of external device 116, clinician IO device 120. Patient IO device 118, network 136, and/or medical devices 108, 122, 144, 150, 156. In some examples, some or substantially all of the functionality ascribed to processing circuitry 114 may be performed by one or more devices and/or circuitries not shown in FIG. 4.

System 100 (e.g., processing circuitry 114) may also be configured to retrieve data regarding patient 102 and/or fetal patient 104 from electronic health records (EHR) via network 136. The EHR may include data regarding historical (e.g., baseline) physiological parameter values, previous health events and treatments, disease states, comorbidities, demographics, height, weight, and body mass index (BMI), as examples, of patients including maternal patient 102 and/or fetal patient 104. System 100 may use data from the EHR to configure algorithms implemented by processing circuitry 114, medical device 108, and/or other devices within system 100 to detect and/or define patient attributes and or attribute signs.

Detection of patient attributes and or attribute signs can be achieved by looking at a number of possible physiological traits that occur prior to and while defining a patient attribute and or attribute sign. The advantageous markers to detect an impending or ongoing event may be determined based on an etiology of the patient. The etiology of patient 102 and/or fetal patient 104 may include baseline characteristics, medical history, or disease state. The etiology may include any EHR data, as well as patient activity level or metabolite level. With such possible inputs, processing circuitry 114 may be configured to determine patient physiological traits to exhibit certain trends or threshold crossings to detect an impending or ongoing acute health event, e.g., one or more of a patient attribute and or attribute sign. In some examples, system 100 may be configured to utilize a set of rules to determine one or more patient attributes and/or attribute signs. System 100 may be configured to modify the rule set to modify certain rules (e.g., turn certain rules on or off), change the weighting of certain rules, or conduct other modifications.

Figure 5:
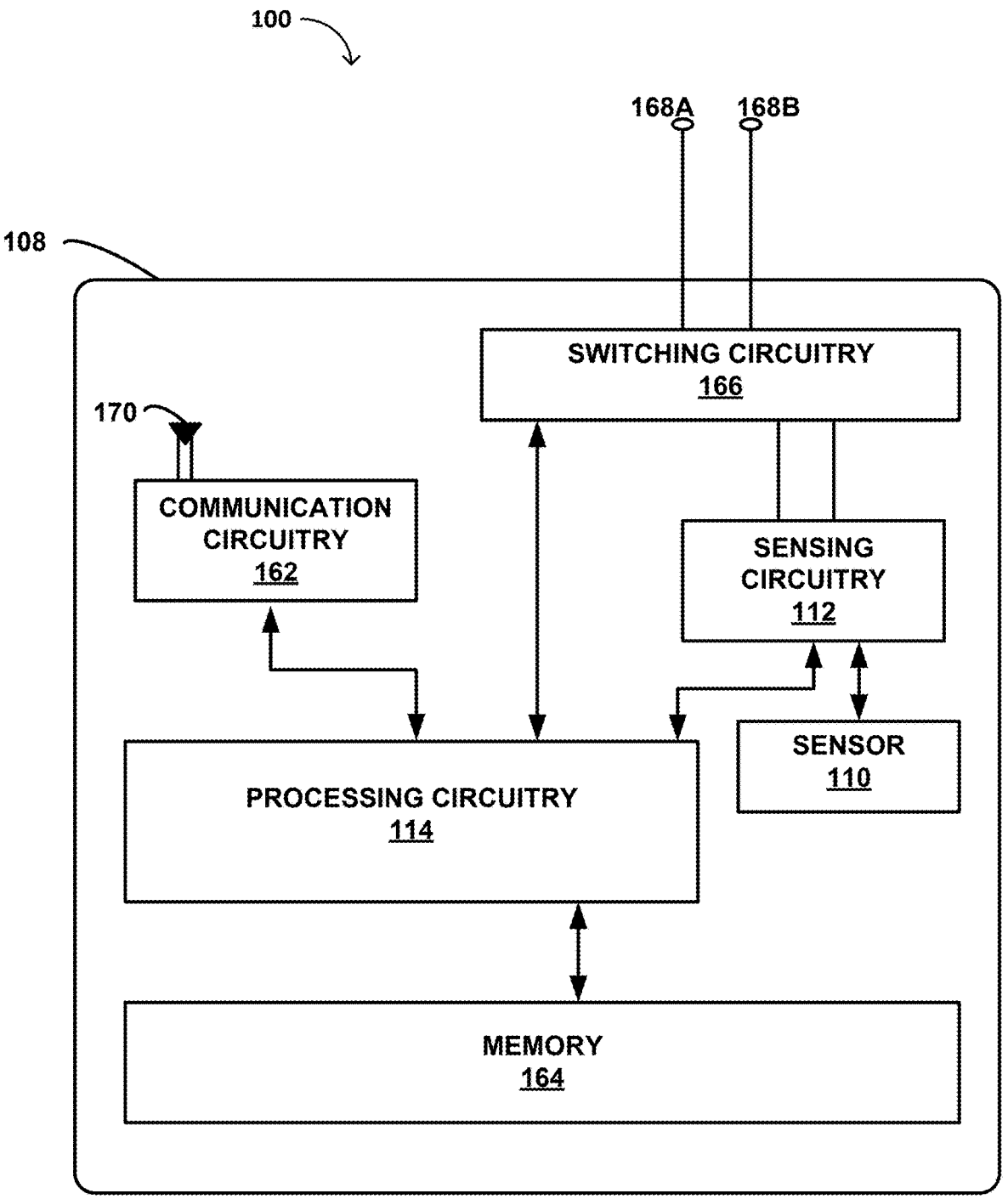
FIG. 5 is a block diagram illustrating circuitry of an example medical device.

FIG. 5 is a block diagram illustrating an example configuration of medical device 108. As shown in FIG. 5, medical device 108 may include at least some portion of processing circuitry 114, sensing circuitry 112, communication circuitry 162, memory 164, one or more sensors such as sensor 110, switching circuitry 166, and sensing element 168A, 168B (hereinafter "sensing elements 168"), one or more of which may be disposed on a housing of medical device 108. In some examples, memory 164 includes computer-readable instructions that, when executed by processing circuitry 114, cause medical device 108 and processing circuitry 114 to perform various functions attributed herein to medical device 108 and processing circuitry 114. Memory 164 may include any volatile, non-volatile, magnetic, optical, or electrical media, such as a random-access memory (RAM), ferro-electric RAM (F-RAM), read-only memory (ROM), non-volatile RAM (NVRAM), electrically-erasable programmable ROM (EEPROM), flash memory, or any other digital media.

Processing circuitry 114 may include fixed function circuitry and/or programmable processing circuitry. Processing circuitry 114 may include any one or more of a microprocessor, a controller, a digital signal processor (DSP), an application specific integrated circuit (ASIC), a field-programmable gate array (FPGA), a tensor processing unit (TPU) and/or other AI processing unit, or equivalent discrete or analog logic circuitry. In some examples, processing circuitry 114 may include multiple components, such as any combination of one or more microprocessors, one or more controllers, one or more DSPs, one or more ASICs, or one or more FPGAs, as well as other discrete or integrated logic circuitry. The functions attributed to processing circuitry 114 herein may be embodied as software, firmware, hardware, or any combination thereof.

Sensing circuitry 112 may be selectively connected to sensing elements 168 via switching circuitry 166 as controlled by processing circuitry 114. Sensing elements 168 may be configured to sense a patient physiological data of patient 102, such as an electrocardiogram ("ECG"), echocardiogram, electromyography, impedance magnitude, optical signal, a pressure, an accelerometry, an audible sound, and/or any other physiological trait influenced by a body and/or body function of patient 102. Sensing elements 158 may include, for example, electrodes, accelerometers, microphones, optical sensors, temperature sensors, force sensors, and/or pressure sensors. Sensing circuitry 112 may monitor signals from sensing elements 168 and provide output signals 134 to processing circuitry 114. Sensing circuitry 112 and/or processing circuitry 114 may include one or more filters and amplifiers for filtering and amplifying signals received from one or more of sensing elements 168 and/or other sensors. In some examples, sensing circuitry 112 and/or processing circuitry 114 may include a rectifier, filter and/or amplifier, a sense amplifier, comparator, and/or analog-to-digital converter. Processing circuitry 114 may define and/or monitor patient physiological data store the patient physiological data in memory 164.

Processing circuitry 114 may issue, via communication circuitry 162, a communication to patient IO device 118, external device 116, and/or clinician IO device 120, based on a comparison of a patient attribute and a attribute sign. Processing circuitry 114 may communicate, via communication circuitry 162, at least a portion of the patient physiological data to patient IO device 118, external device 116, and/or clinician IO device 120. Such transmissions may occur on a daily or other basis. Communication circuitry 162 may include any suitable hardware, firmware, software, or any combination thereof for communicating with another device, such as computing devices 12, with the aid of an internal or external antenna, e.g., antenna 170.

Medical device 108 may be any device configured to sense a physiological trait of patient 102 and communicate patient physiological data. In examples, medical device 108 may include a leadless, subcutaneously-implantable monitoring device configured to be implanted with patient 102. Medical device 108 may be a device configured to substantially non-invasively contact a body of patient 102 to position sensor 110 (e.g., smartwatch and/or other smart apparel). Medical device 108 may be a device configured to position sensor 110 through a manipulation by and/or action of patient 102 (e.g., a weight scale, a blood pressure cuff, and/or a glucose testing device). Although described primarily in the context of examples in which medical device 108 takes the form of a device configured to be implanted within patient 102, the medical device 108 may be any device configured to position sensor 110 such that sensor 110 may to sense a physiological trait of patient 102. As discussed, the physiological trait of patient 102 may include a fetal physiological trait of fetal patient 104 (FIG. 3).

Figure 6:
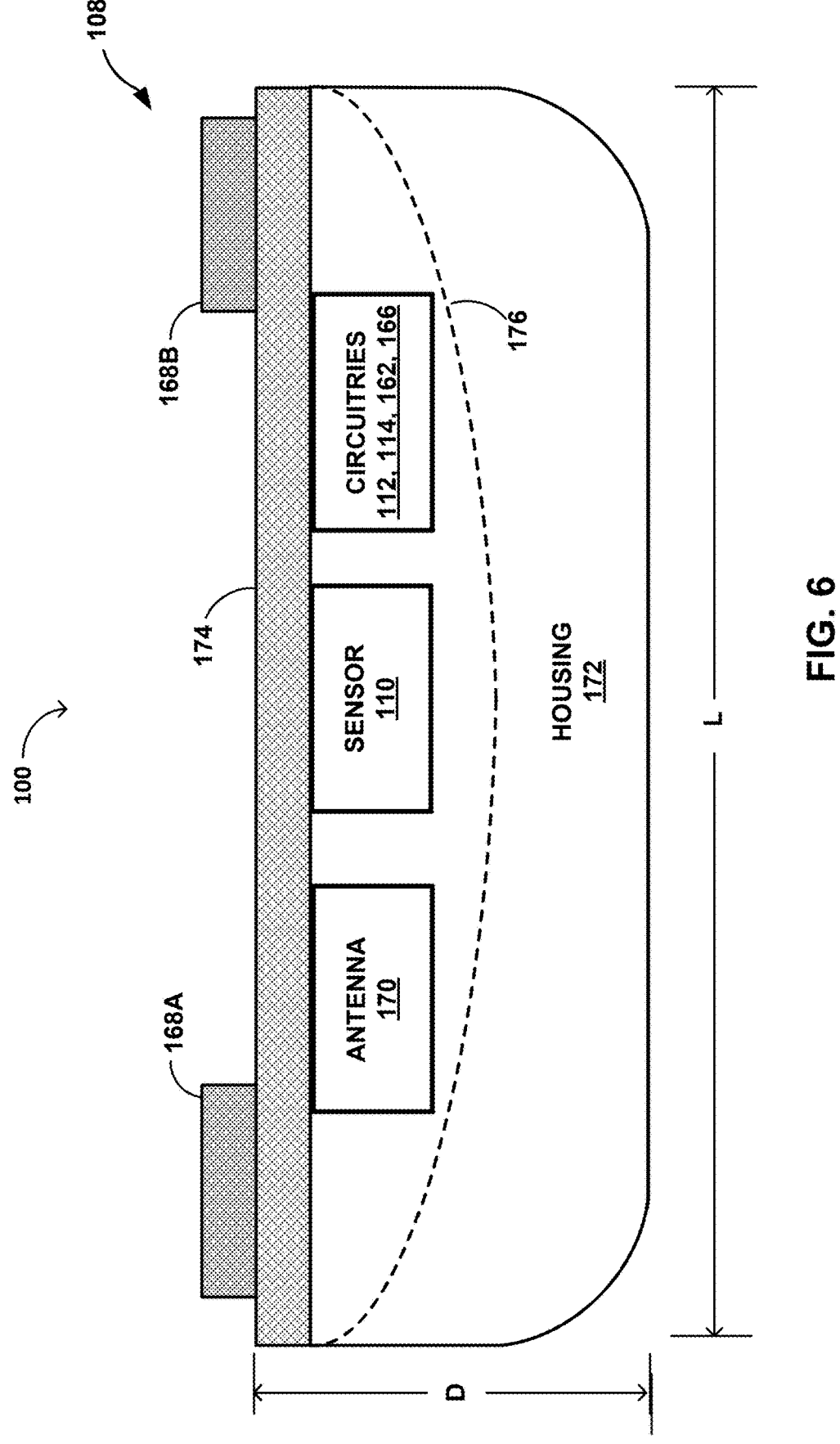
FIG. 6 is a schematic diagram illustrating an example medical device.

FIG. 6 is a conceptual side-view diagram illustrating an example configuration of medical device 108. In the example shown in FIG. 6, medical device 108 may include a housing 172 and a cover 174 mechanically supported by housing 172. Cover 174 may be an insulative cover. Sensing element 168A and sensing element 168B may be formed on or placed on an outer surface of cover 174, or otherwise in mechanical communication with cover 174. Circuitries 112, 114, 162, 166, described above with respect to FIGS. 1-4, may be formed on, placed within, and/or otherwise mechanically supported by an inner surface of cover 74, or within housing 72. Antenna 170 may be mechanically supported by, formed on, or placed within housing 172 and/or cover 174. In some examples, cover 74 may be positioned over an opening defined by housing 172, such that housing 172 and cover 174 enclose antenna 170, sensing elements 168, sensor 110, and/or circuitries 112, 114, 162, 166. Housing 172 and cover 174 may enclose antenna 170, sensing elements 168, sensor 110, and/or circuitries 112, 114, 162, 166 to, for example, protect antenna 170, sensing elements 168, sensor 110, and/or circuitries 112, 114, 162, 166 from fluids such as body fluids.

One or more of antenna 170, sensing elements 168, sensor 110, and/or circuitries 112, 114, 162, 166 may be formed on cover 174, such as by using flip-chip technology. Cover 174 may be flipped onto a housing 172. When flipped and placed onto housing 172, the components of medical device 108 formed on the inner side of cover 174 may be positioned in a gap 176 defined by housing 172. Sensing elements 168 may be electrically connected to switching circuitry 166 through one or more vias (not shown) formed through cover 174. Cover 174 may be formed of sapphire (i.e., corundum), glass, parylene, and/or any other suitable material. Housing 172 may be formed from titanium or any other suitable material (e.g., a biocompatible material). Sensing elements 168 (e.g., an electrode) may be formed from any of stainless steel, titanium, platinum, iridium, alloys thereof, or other suitable materials. In addition, sensing elements 168 may be coated with a material such as titanium nitride or fractal titanium nitride, although other suitable materials and coatings for such electrodes may be used.

In the example shown in FIG. 6, the housing 172 of medical device 108 defines a length L and a thickness or depth D and is in the form of an elongated rectangular prism wherein the length L is larger than the depth D. Housing 172 may define a width W perpendicular to the length L and perpendicular to the depth D (e.g. proceeding into the page). In examples, the width W is larger than the depth D. For example, the spacing between sensing element 168A and sensing element 168B may range from 30 millimeters (mm) to 50 mm, from 35 mm to 45 mm, or be approximately 40 mm. In addition, in some examples, length L may range from 30 mm to about 70 mm. In other examples, the length L may range from 5 mm to 60 mm, 40 mm to 60 mm, 45 mm to 55 mm, or be approximately 45 mm. In addition, in examples, the width W may range from 3 mm to 15 mm, such as approximately 8 mm. In some examples, depth D may range from 2 mm to 15 mm, from 3 to 5 mm, or be approximately 4 mm. In some examples, medical device 108 may have a volume of three cubic centimeters (cm) or less, or 1.5 cubic cm or less, such as approximately 1.4 cubic cm.

Figure 7:
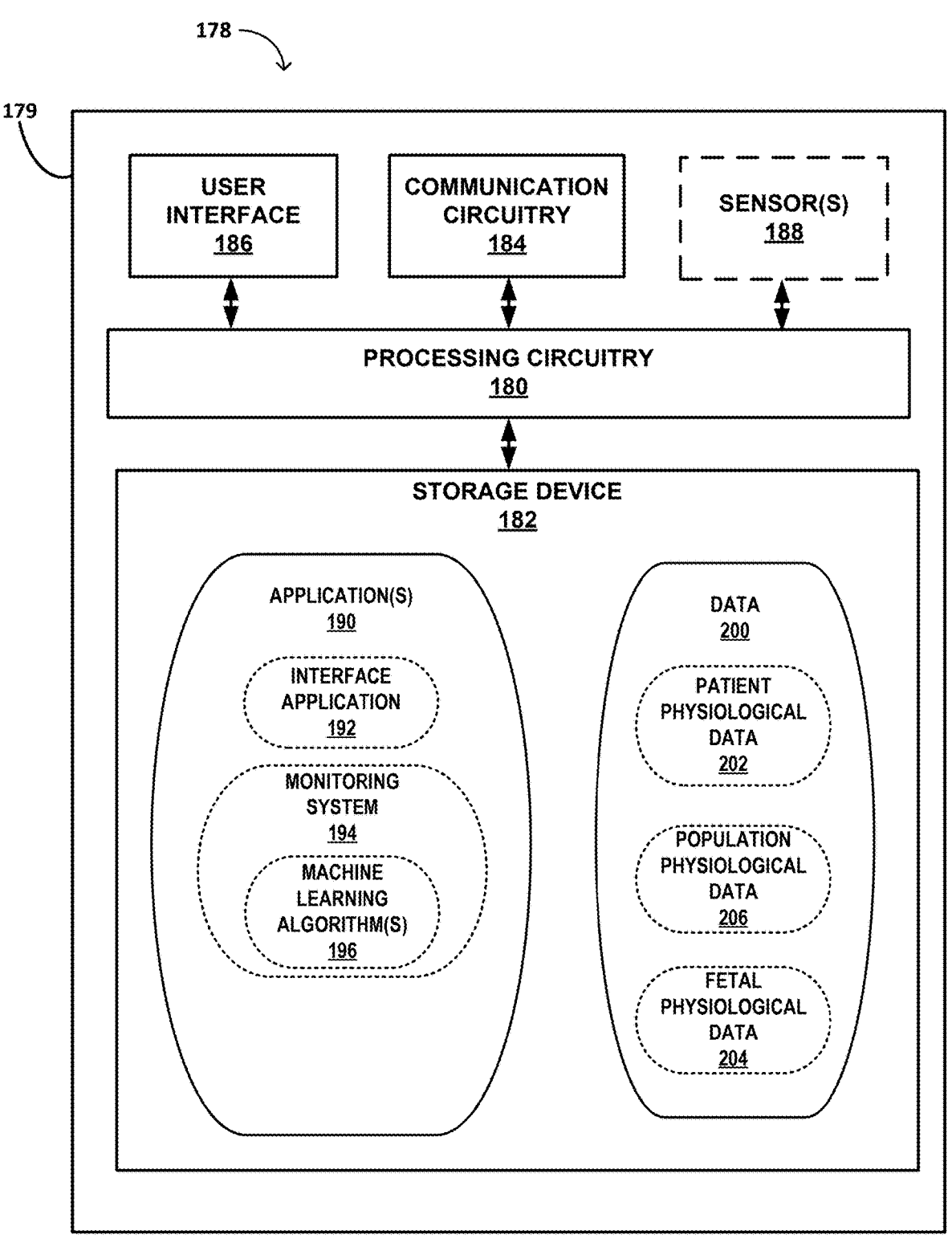
FIG. 7 is a block diagram illustrating an example configuration of a computing device that operates in accordance with one or more techniques of the present disclosure.

FIG. 7 is a block diagram illustrating an example configuration of a computing device 178 which may be an example of external device 116, clinician IO device 120, patient IO device 118, and/or medical devices 108, 122, 144, 150, 156. In some examples, computing device 178 takes the form of a smartphone, a laptop, a tablet computer, a personal digital assistant (PDA), a smartwatch or other wearable computing device, smart home appliance, such as a smart speaker, or any IoT device. As shown in the example of FIG. 7, computing device 178 includes processing circuitry 180, storage device 182, communication circuitry 184, a user interface 186 and, in some examples, one or more sensors 188. Processing circuitry 180 may include at least some portion of processing circuitry 114 (FIGS. 1-5). Storage device 182 may include at least some portion of memory 164 (FIG. 5). Communication circuitry 184 may include at least some portion of communication circuitry 162 (FIG. 5). Sensors 188 may include at least some portion of sensor 110 (FIG. 1-5). Although shown in FIG. 7 as a stand-alone device for purposes of example, computing device 178 may be any component or system that includes processing circuitry or other suitable computing environment for executing software instructions and, for example, need not necessarily include one or more elements shown in FIG. 7 (e.g., in some examples components such as storage device 182 may not be co-located or in the same chassis as other components).

Processing circuitry 180, in one example, is configured to implement functionality and/or process instructions for execution within computing device 178. For example, processing circuitry 180 may be capable of processing instructions, including applications 190, stored in storage device 182. Examples of processing circuitry 180 may include, any one or more of a microprocessor, a controller, a digital signal processor (DSP), an application specific integrated circuit (ASIC), a field-programmable gate array (FPGA), a tensor processing unit (TPU) and/or other AI processing unit, or equivalent discrete or integrated logic circuitry.

Storage device 182 may be configured to store information within computing device 178, including applications 190 and data 200. Data 200 may include patient physiological data 202 and/or population physiological data 206. In examples, data 200 may include fetal physiological data 204 (e.g., based on the one or more physiological traits of patient 102). Storage device 182, in some examples, is described as a computer-readable storage medium. In some examples, storage device 182 includes a temporary memory or a volatile memory. Examples of volatile memories include random access memories (RAM), dynamic random access memories (DRAM), static random access memories (SRAM), and other forms of volatile memories known in the art. Storage device 182, in one example, is used by applications 190 running on computing device 178 to temporarily store information during program execution. Storage device 182, in some examples, also includes one or more memories configured for long-term storage of information, e.g., including non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 178 utilizes communication circuitry 184 to communicate with other devices, such as external device 116, clinician IO device 120, patient IO device 118, and/or medical device 108. Communication circuitry 184 may include a network interface card, such as an Ethernet card, an optical transceiver, a radio frequency transceiver, or any other type of device that can send and receive information. Other examples of such network interfaces may include 3G, 4G, 5G, LoRaWAN, and WiFi radios.

Computing device 178 also includes a user interface 186. User interface 186 may be configured to provide output to a user using tactile, audio, or video stimuli and receive input from a user through tactile, audio, or video feedback. User interface 186 may include, as examples, a presence-sensitive display, a mouse, a keyboard, a voice responsive system, video camera, microphone, or any other type of device for detecting a command from a user, a sound card, a video graphics adapter card, or any other type of device for converting a signal into an appropriate form understandable to humans or machines, a speaker, a cathode ray tube (CRT) monitor, a liquid crystal display (LCD), or any other type of device that can generate intelligible output to a user. In some examples, a presence-sensitive display includes a touch-sensitive screen.

Example applications 190 executable by processing circuitry 180 of computing device 178 may include an interface application 192 configured to facilitate a user interface with, for example, clinician IO device 120, patient IO device 118, external device 116, and/or medical device 108. Example applications 190 may include a monitoring system 194 that may utilize one or more machine learning algorithms 196. Execution of interface application 192 by processing circuitry 180 may configure computing device 178 to interface with clinician IO device 120, patient IO device 118, external device 116, and/or medical device 108. For example, interface application 192 may configure computing device 178 to communicate with clinician IO device 120, patient IO device 118, external device 116, and/or medical device 108 via communication circuitry 184. Processing circuitry 180 may receive patient physiological data 202 and/or fetal physiologic data 204 from medical device 108 and/or population physiological data 206 from medical devices 144, 150, 156, and store patient physiological data 202, fetal physiological data 204, and/or population physiological data in storage device 182. Interface 192 application may also configure user interface 186 for a user to interact with data 200, and/or interact with clinician IO device 120, patient IO device 118, external device 116, and/or medical device 108. Processing circuitry 180 may execute monitoring system 194 to facilitate monitoring the health of patient 102 and/or fetal patient 104, e.g., based on data 200 and/or other data collected by computing device 178. Monitoring system 194 may cause processing circuitry 180 and computing device 178 to perform any of the techniques described herein related to the patient physiological data of patient 102 and/or the fetal physiologic data of fetal patient 104.

In some examples, processing circuitry 180 executes monitoring system 194 to define a patient attribute. Processing circuitry 180 may execute monitoring system 194 to define and/or redefine an attribute sign. Processing circuitry 180 may execute monitoring system 194 to gather patient physiological data 202, fetal physiological data 204, and/or population physiological data 206. Processing circuitry 180 may execute monitoring system 194 define a patient parameter based on patient physiological data 202. Processing circuitry 180 may execute monitoring system 194 to define a training data set and/or population training data set and train machine learning algorithm 196 using the training data set and/or population training data set. Processing circuitry 180 may execute monitoring system 194 to perform any of the techniques described herein for medical system 100.

In some examples, computing device 178 includes a housing 179 mechanically supporting and/or at least partially enclosing substantially all or at least some part of circuitry and/or other components configured to perform functions ascribed to processing circuitry 180, storage device 182, communication circuitry 184, user interface 186, sensors 188, applications 190, interface application 192, monitoring system 194, machine learning algorithms 196, data 200, patient physiological data 202, fetal physiological 204, and/or population physiological data 206.

Figure 8:
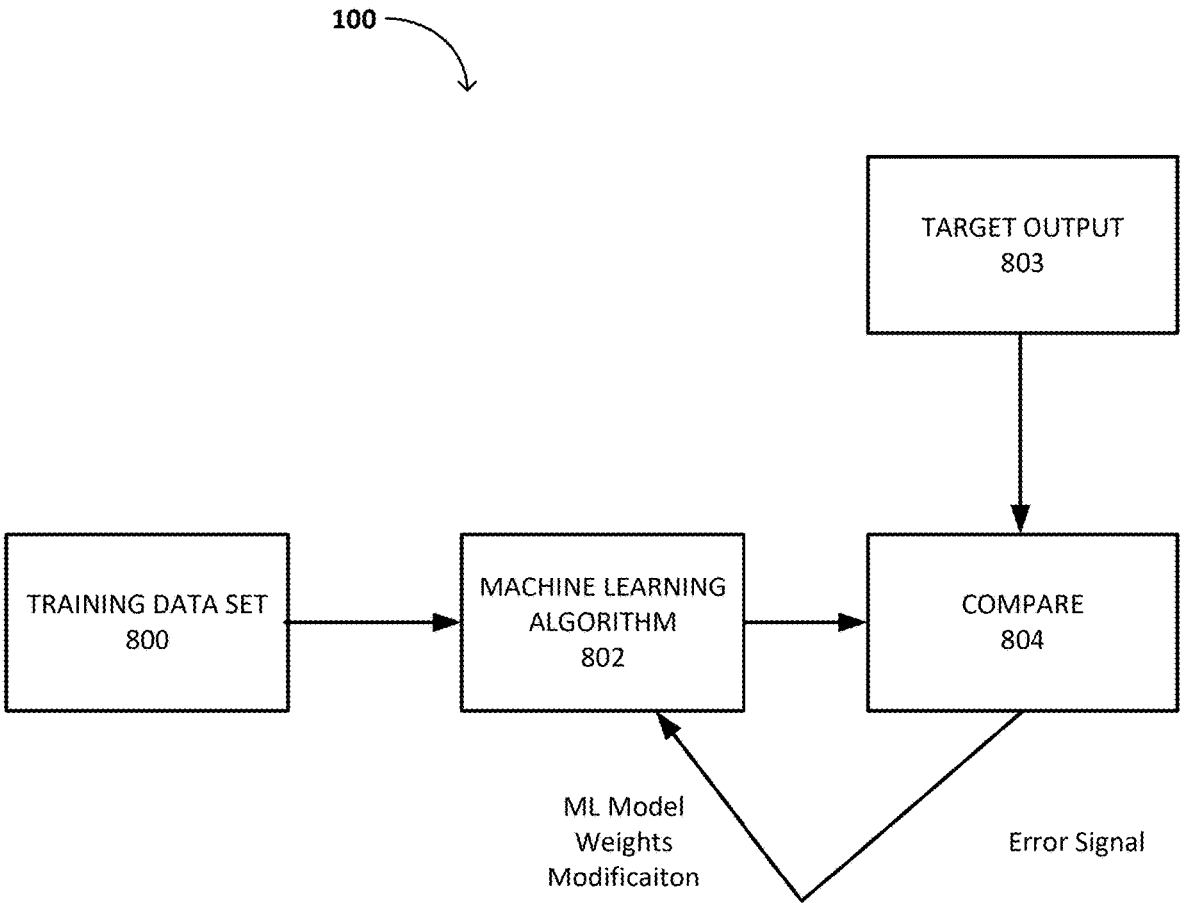
FIG. 8 is a conceptual diagram illustrating an example training process for a machine learning algorithm, in accordance with examples of the current disclosure.

FIG. 8 is an example of a machine learning algorithm 802 being trained using supervised and/or reinforcement learning techniques. The machine learning algorithm 802 may be implemented using any number of models for supervised and/or reinforcement learning, such as but not limited to, an artificial neural network, a decision tree, naïve Bayes network, support vector machine, or k-nearest neighbor model, to name only a few examples. In some examples, one or more of medical device 108, second medical device 122, processing circuitry 114, external device 116, clinician IO device 120, and/or patient input/output device 118 initially trains the machine learning algorithm 802 using a training data set 800. Training data set 800 may include training input vectors indicative of patient physiological data, wherein one or more elements in a training input vector may be representative of physiological traits, patient attributes, and/or other physiological data. In examples, training data set 800 includes population input vectors indicative of population physiological data, wherein one or more elements in a population input vector may be representative of physiological traits and/or attributes of other individual patients. Each of the training input vectors and/or each of the population input vectors may be associated with a training output vector to define a data pair.

One or more of medical device 108, second medical device 122, processing circuitry 114, external device 116, clinician IO device 120, and/or patient input/output device 118 may select training data set 800 comprising a set of data pairs. A prediction by the machine learning algorithm 802 may be compared 804 to a target output 803 (e.g., a target output described by a training output vector), and an error signal and/or machine learning model weights modification may sent/applied to machine learning algorithm 802 based on the comparison to modify/update machine learning model 802. For example, one or more of medical device 108, second medical device 122, processing circuitry 114, external device 116, clinician IO device 120, and/or patient input/output device 118 may, for each training instance in the training set, modify machine learning model 802 to change a score generated by machine learning model 802 in response to subsequent input vectors applied to machine learning algorithm 802. In examples, the error signal and/or machine learning model weights modification modifies and/or alters the mapping of a subsequent training vector onto an output space defined by one or more training output vectors.

Figure 9:
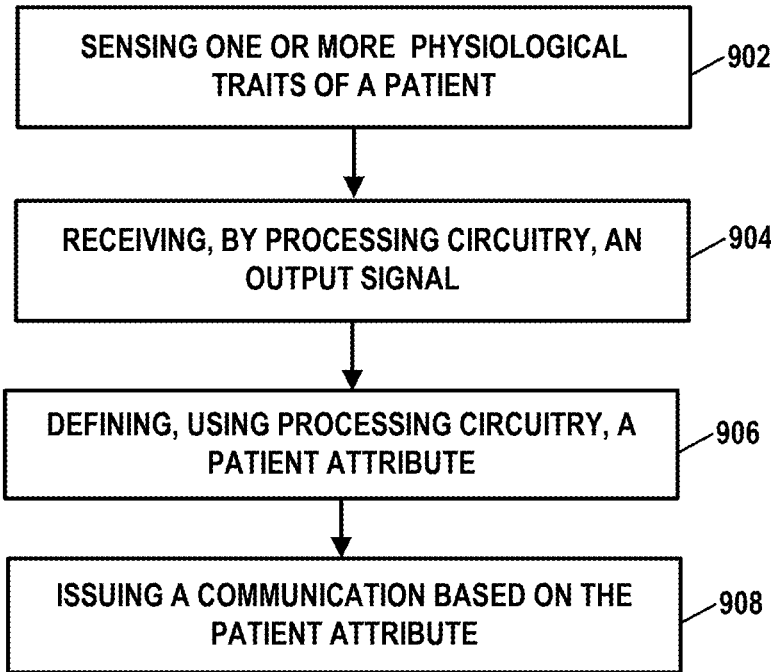
FIG. 9 is a flow diagram illustrating an example technique for monitoring a physiological trait of a patient for an obstetric condition.

FIG. 9 is a flow diagram illustrating an example technique for sensing physiological attributes of a patient to monitor a patient for an obstetric condition. Although the technique is described mainly with reference to medical system 100 of FIGS. 1-8, the technique may be performed by other medical systems in other examples.

The technique includes sensing one or more physiological traits of a patient 102 using one or more sensors 110, 124, 188 (902). The one or more physiological traits are indicative of one or more patient attributes of patient 102. The one or more physiological traits of patient 102 may include one or more physiological traits indicative of a fetal attribute of a fetal patient 104 carried by patient 102. The one or more patient attributes of patient 102 may include one or more fetal attributes of fetal patient 104. The patient attribute is indicative of a physiological characteristic of a body and/or body function of patient 102. In examples, the patient attribute at least one of a hormone level of patient 102, a heart rate of patient 102, a systolic blood pressure of patient 102, a diastolic blood pressure of patient 102, an oxygen saturation level of patient 102, a respiration rate of patient 102, a temperature of patient 102, a muscle contraction of patient 102, a blood glucose level of patient 102, and/or a weight of patient 102. The patient attribute may include at least one of a heart rate of fetal patient 104, a systolic blood pressure of fetal patient 104, a diastolic blood pressure of fetal patient 104, an oxygen saturation level of fetal patient 104, a respiration rate of fetal patient 104, and/or a temperature of fetal patient 104.

The physiological trait sensed may be an electrocardiogram of patient 102, an echocardiogram of patient 102, an audible sound generated by patient 102, an accelerometer signal indicative of a movement of patient 102, an electromyography signal indicative of a muscle contraction of patient 102, an oxygen saturation signal indicative of an oxygen saturation of patient 102, an optical signal influenced by the body of patient 102, and/or another physiological trait. In some examples, sensors 110, 124, 188 sense a mixed physiological trait indicative of both a first patient attribute and a second fetal attribute. In some examples, sensors 110, 124, 188 sense the first physiological attribute using a first sensor and sense the second physiological attribute using a second sensor. In examples, the first physiological trait and/or the second physiological trait includes a fetal physiological trait of fetal patient 104.

The technique includes receiving, by processing circuitry 114, 180 output signals 134 generated by sensing circuitry 112, 126, operably connected to sensors 110, 124, 188 (904). Output signals 134 are indicative of the patient attribute. The technique includes defining, using processing circuitry 114, 180 the patient attribute using output signals 134 (906). In examples, output signals 134 may include a first output signal indicative of a first patient attribute and a second output signal indicative of a second patient attribute, and processing circuitry 114, 180 defines the first patient attribute using the first output signal and defines the second patient attribute using the second output signal. In examples, output signals 134 includes a mixed output signal indicative of both the first patient attribute and the second patient attribute, and processing circuitry 114, 180 defines the first patient attribute and the second patient attribute using the mixed output signal. Processing circuitry 114, 180 may perform a signal separation technique to define the first patient attribute and the second patient attribute. In examples, the first patient attribute and/or the second patient attribute includes a fetal attribute of fetal patient 104.

The technique includes issuing a communication, using processing circuitry 114, 180 based on a comparison of the patient attribute and a attribute sign. (908). Processing circuitry 114, 180 may convey the communication using communications circuitry 162, 184. Processing circuitry 114, 180 may issue the communication to device circuitry of at least one of patient input/output device 118, external device 116, and/or clinician IO device 120. In examples, processing circuitry 114, 180 communicates data indicative of at least one of the physiological trait, a patient physiological parameter indicative of the physiological trait, and/or the patient attribute, to device circuitry of at least one of a patient input/output device 118, external device 116, and/or clinician IO device 120. Processing circuitry 114, 180 may communicate data indicative of at least one of the fetal physiological trait, a fetal physiological parameter indicative of the fetal physiological trait, or the fetal attribute to device circuitry of at least one of a patient input/output device 118, external device 116, and/or clinician IO device 120.

Processing circuitry 114, 180 may compare the patient attribute to an attribute sign which describes a threshold for an obstetric condition of patient 102. In examples, the patient attribute is indicative of a hormone level of patient 102 and the obstetric condition of patient 102 is one of a maximum hormone level for the obstetric condition or a minimum hormone level for the obstetric condition. In examples, the patient attribute is indicative of a heart rate of patient 102 and the obstetric condition of patient 102 is one of a maximum heart rate for the obstetric condition or a minimum heart rate for the obstetric condition. In examples, the patient attribute is indicative of a systolic blood pressure of patient 102 and the obstetric condition of patient 102 is one of a maximum systolic blood pressure for the obstetric condition or a minimum systolic blood pressure rate for the obstetric condition. In examples, the patient attribute is indicative of a diastolic blood pressure of patient 102 and the obstetric condition of patient 102 is one of a maximum diastolic blood pressure for the obstetric condition or a minimum diastolic blood pressure for the obstetric condition. In examples, the patient attribute is indicative of an oxygen saturation level of patient 102 and the obstetric condition of patient 102 is one of a maximum oxygen saturation level for the obstetric condition or a minimum oxygen saturation level for the obstetric condition. In examples, the patient attribute is indicative of a respiration rate of patient 102 and the obstetric condition of patient 102 is one of a maximum respiration rate for the obstetric condition or a minimum respiration rate for the obstetric condition. In examples, the patient attribute is indicative of a temperature of patient 102 and the obstetric condition of patient 102 is one of a maximum temperature for the obstetric condition or a minimum temperature for the obstetric condition. In examples, the patient attribute is indicative of an activity level of patient 102 and the obstetric condition of patient 102 is one of a maximum activity level for the obstetric condition or a minimum activity level for the obstetric condition. In examples, the patient attribute is indicative of a muscle contraction of patient 102 and the obstetric condition of patient 102 is one of false labor for the obstetric condition or maternal labor for the obstetric condition. In examples, the patient attribute is indicative of a blood glucose level of patient 102 and the obstetric condition of patient 102 is one of a maximum blood glucose level for the obstetric condition (e.g., a maximum blood glucose level indicative of gestational diabetes) or a minimum blood glucose level for the obstetric condition. In examples, the patient attribute is indicative of a weight of patient 102 and the obstetric condition of patient 102 is one of a maximum weight for the obstetric condition or a minimum weight for the obstetric condition. In examples, the patient attribute is indicative of a fluid level of patient 102 and the obstetric condition of patient 102 is one of a maximum fluid level for the obstetric condition or a minimum fluid level for the obstetric condition.

In examples, the patient attribute is indicative of one or more of a heart rate of fetal patient 104, a systolic blood pressure of fetal patient 104, a diastolic blood pressure of fetal patient 104, an oxygen saturation level of fetal patient 104, a respiration rate of fetal patient 104, a temperature of fetal patient 104, and/or an activity level of fetal patient 104. The obstetric condition may be one or more of a maximum heart rate of fetal patient 104, a minimum heart rate of fetal patient 104, maximum systolic blood pressure of fetal patient 104, a minimum systolic blood pressure of fetal patient 104, maximum diastolic blood pressure of fetal patient 104, a minimum diastolic blood pressure rate of fetal patient 104, a maximum oxygen saturation level of fetal patient 104, a minimum oxygen saturation level of fetal patient 104, a maximum respiration rate of fetal patient 104, a minimum respiration rate of fetal patient 104, a maximum temperature of fetal patient 104, a minimum temperature of fetal patient 104, a maximum activity level of fetal patient 104, or a minimum activity level of fetal patient 104.

In examples, processing circuitry 114, 180 issues the communication using a tiered communication indicative of an assessment of the comparison of the patient attribute and the attribute sign. Processing circuitry 114, 180 may define a tier of a communication based on a plurality of attribute signs (e.g., a first attribute sign, a second attribute sign, and/or a third attribute sign). In examples, processing circuitry 114, 180 issues a Tier I communication when the patient attribute is assessed to be a normally expected value (e.g., within a range defined by the first attribute sign). Processing circuitry 114, 180 may issue a Tier II communication when the patient attribute is assessed to potentially indicate a condition warranting further evaluation and/or action by patient 102 and/or a clinician (e.g., within a range defined by the second attribute sign.) Processing circuitry 114, 180 may issue a Tier III communication when the patient attribute is assessed to indicate a condition potentially more serious and/or warranting more urgent action and/or action by patient 102 and/or the clinician (e.g., within a range defined by the third attribute sign).

The tiered communication system may define any number of tiers and any number of attribute signs. In some examples, processing circuitry 114 causes patient IO device 118 and/or clinician IO device 120 to provide visible, audible, or other indicia associated with a tier of the communication. For example, processing circuitry 114 may cause patient IO device 118 and/or clinician IO device 120 to provide a first indicia (e.g., a green background) for a Tier I communication, a second indicia (e.g., a yellow background) for a Tier II communication, and/or a third indicia (e.g., a red background) for a Tier III communication. In examples, processing circuitry 114, 180 may select and/or communicate one or more treatment recommendations based on the communication.

Processing circuitry 114, 180 may define and/or refine the attribute sign to reduce a rate of false positives when comparing the patient attribute to the attribute sign. Processing circuitry 114, 180 may utilize patient physiological data to define and/or refine the attribute sign. In examples, processing circuitry 114, 180 uses a machine learning algorithm 196 trained with a training data set based on the patient physiological data. Machine learning algorithm 196 may define and/or refine the attribute sign using the patient physiological data. In examples, medical system 100 receives an assessment input from patient input/output device 118, external device 116, and/or clinician IO device 120, or another input device. Machine learning algorithm 196 may be trained using a training data set including the assessment input. In some examples, processing circuitry 114, 180 may define and/or refine the attribute sign based on population data sensed from a population of other individual patients 148, 154, 160. Processing circuitry 114, 180 may utilize machine learning algorithm 196 to define and/or refine the attribute sign using the population data. Processing circuitry 114, 180 may communicate with individual medical devices 144, 150, 156 to gather the population data.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), tensor processing units (TPUs) and/or other AI processing units, or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The disclosure includes the following examples.

Example 1: A system comprising: one or more sensors configured to sense one or more physiological traits indicative of one or more patient attributes of a patient, wherein the one or more patient attributes are indicative of one or more physiological characteristics of a body of the patient; sensing circuitry operably connected to the one or more sensors and configured to issue one or more output signals indicative of the one or more physiological traits; and processing circuitry operably connected to the sensing circuitry, wherein the processing circuitry is configured to: receive the one or more output signals from the sensing circuitry, define the one or more patient attributes using the one or more received output signals, and issue a communication based on a comparison of the one or more patient attributes and an attribute sign, wherein the attribute sign includes a threshold for the patient attribute, wherein the attribute sign is indicative of an obstetric condition defined by the one or more of the physiological characteristics, and wherein the obstetric condition is indicative of a fertility phase of the patient, a pregnancy of the patient, labor of the patient, or a postpartum condition of the patient.

Example 2: The system of example 1, wherein: the one or more sensors are configured to sense a plurality of physiological traits indicative of a plurality of physiological characteristics, the one or more output signals are indicative of the plurality of physiological traits, the processing circuitry is configured to define a plurality of patient attributes using the received one or more output signals, and the processing circuitry is configured to issue the communication based on a comparison of the plurality of patient attributes and the attribute sign, wherein the attribute sign is indicative of an obstetric condition defined by the plurality of physiological characteristics.

Example 3: The system of examples 1 or 2, wherein the one or more sensors are configured to sense a first physiological trait indicative of a first attribute and a second physiological trait indicative of a second attribute, and wherein the patient attribute is based on at least the first attribute and the second attribute.

Example 4: The system of example 3, wherein: the one or more sensors includes at least a first sensor configured to sense the first attribute and a second sensor is configured to sense the second attribute, the one or more output signals includes a first output signal from first sensing circuitry of the first sensor and a second output signal from second sensing circuitry of the second sensor, and the processing circuitry is configured to define the one or more patient attributes using the first output signal and the second output signal.

Example 5: The system of any of examples 1-4, wherein the one or more patient attributes is one or more of a heart rate, a hormone level, a temperature, a systolic blood pressure, a diastolic blood pressure, an oxygen saturation level, a respiration rate, a muscle contraction, a blood glucose level, a weight, an activity level, or a fluid level.

Example 6: The system of any of examples 1-5, wherein the processing circuitry is configured to define the one or more patient attributes based on the obstetric condition.

Example 7: The system of example 6, wherein the processing circuitry is configured to receive an indication of the obstetric condition from a user input device.

Example 8: The system of any of examples 1-7, wherein the processing circuitry is configured to direct the one or more sensors to sense the one or more physiological traits based on the obstetric condition.

Example 9: The system of any of examples 1-8, wherein the processing circuitry is configured to identify the obstetric condition based on the comparison of the one or more patient attributes and the attribute sign.

Example 10: The system of any of examples 1-8, wherein the processing circuitry is configured to issue the communication to device circuitry of a patient input/output device to cause the patient input/output device to provide an output sensible by the patient, a clinician, or another user when the processing circuitry issues the communication.

Example 11: The system of any of examples 1-10, wherein the processing circuitry is configured to communicate physiological data indicative of at least one of the one or more physiological traits or the one or more patient attributes to device circuitry of a patient input/output device.

Example 12: The system of any of examples 1-11, wherein the processing circuitry is configured to communicate physiological data indicative of at least one of the one or more physiological traits or the one or more patient attributes to device circuitry of at least one of a clinician input/output device or an external device communicatively connected to the clinician input/output device.

Example 13: The system of any of examples 1-12, wherein at least one of the one or more sensors and at least some portion of the sensing circuitry are mechanically supported by a housing of a medical device.

Example 14: The system of example 13, wherein at least some portion of the processing circuitry is mechanically supported by the housing of the medical device.

Example 15: The system of example 13 or 14, wherein at least a first portion of the processing circuitry is mechanically supported by a housing of an external device, wherein the housing of the medical device is displaced from the housing of the external device.

Example 16: The system of any of examples 1-15, further comprising a medical device configured to contact a body of the patient, wherein the medical device mechanically supports the sensor and at least some portion of the sensing circuitry.

Example 17: The system of example 16, wherein the medical device is an implantable medical device configured to implant within the body of the patient.

Example 18: The system of any of examples 1-17, wherein the processing circuitry is configured to select treatment recommendations based on the communication.

Example 19: The system of example 18, wherein the processing circuitry is configured to communicate the treatment recommendations to device circuitry mechanically supported by a patient input/output device to cause the patient input/output device to provide an output sensible by the patient, a clinician, or another user indicative of the treatment recommendations.

Example 20: The system of any of examples 1-19, wherein the attribute sign comprises a plurality of individual attribute signs, and wherein the processing circuitry is configured to issue the communication based on a comparison of the patient attribute and an individual attribute sign, wherein the communication is indicative of the individual attribute sign.

Example 21: The system of any of examples 1-20, wherein the attribute sign includes a first attribute sign for the obstetric condition and a second attribute sign for the obstetric condition, wherein the first attribute sign is different from the second attribute sign, and wherein the processing circuitry is configured to issue a tier I patient communication based on a comparison of the patient attribute and the first attribute sign and issue a tier II patient communication based on a comparison of the patient attribute and the second attribute sign.

Example 22: The system of example 21, wherein the attribute sign includes a third attribute sign for the obstetric condition, wherein the third attribute sign is different from the first attribute sign and the second attribute sign, and wherein the processing circuitry is configured to issue a tier III patient communication based on a comparison of the patient attribute and the third attribute sign.

Example 23: The system of example 21 or example 22, wherein the processing circuitry is configured to issue at least one of the tier I patient communication, the tier II patient communication, or the tier III patient communication, to at least one of device circuitry of a patient input/output device or device circuitry of an external device.

Example 24: The system of any of examples 1-23, wherein the processing circuitry is configured to compare the patient attribute to the attribute sign using a machine learning algorithm.

Example 25: The system of example 24, wherein the processing circuitry is configured to receive an input from a clinician input/output device, wherein the input is indicative of an assessed risk to the patient when the processing circuitry issued a previously issued communication and a previously defined patient attribute.

Example 26: The system of example 25, wherein the machine learning algorithm is trained using a training data set indicative of the previously defined patient attribute and the indicative input.

Example 27: The system of example 26, wherein the processing circuitry is configured to update the training set of the machine learning algorithm based on at least one of the previously defined patient attribute or the indicative input.

Example 28: The system any of examples 1-23, wherein the processing circuitry is configured to: receive an input from a clinician input/output device, wherein the input is indicative of an assessed risk to the patient when the processing circuitry issued a previously issued communication and a previously defined patient attribute, and define the attribute sign using a machine learning algorithm, wherein the machine learning algorithm is trained using a training data set indicative of the previously defined patient attribute and the indicative communication.

Example 29: The system of any of examples 1-28, wherein the processing circuitry is configured to define the attribute sign using a machine learning algorithm, wherein the machine learning algorithm is trained using population data sensed from a population of other patients.

Example 30: The system of any of examples 1-29, wherein: the one or more sensors includes a sensor mechanically supported by a first housing and a sensor mechanically supported by a second housing, and the first housing is configured to contact a body of the maternal patient at a first anatomical location and the second housing is configured to contact the body of the maternal patient at second anatomical location.

Example 31: The system of any of examples 1-29, wherein: the one or more physiological traits include one or more fetal physiological traits indicative of one or more fetal attributes of a fetal patient carried by the patient, the one or more fetal attributes are indicative of one or more physiological characteristics of the fetal patient, the one or more patient attributes includes the one or more fetal attributes, and the attribute sign is indicative of an obstetric condition defined by the one or more physiological characteristics of the fetal patient.

Example 32: The system of example 31, wherein the one or more output signals is a mixed output signal indicative of the one or more physiological traits including the one or more fetal physiological traits, and wherein the processing circuitry is configured to define the one or more fetal attributes using the mixed output signal.

Example 33: The system of examples 1-32, wherein the one or more physiological traits are indicative of a body temperature, and wherein the attribute sign defines at least one of a maximum temperature for the obstetric condition or a minimum temperature for the obstetric condition.

Example 34: The system of examples 1-33, wherein the one or more physiological traits are indicative of a hormone level, and wherein the attribute sign defines at least one of a maximum hormone level for the obstetric condition or a minimum hormone level for the obstetric condition.

Example 35: The system of any of examples 1-34, wherein the one or more physiological traits are indicative of a muscle contraction, and wherein the attribute sign defines at least one of a maximum muscle contraction for the obstetric condition or a minimum muscle contraction for the obstetric condition.

Example 36: The system of any of examples 1-35, wherein the one or more physiological traits are indicative of a heart rate, and wherein the attribute sign defines at least one of a maximum heart rate for the obstetric condition or a minimum heart rate for the obstetric condition.

Example 37: The system of any of examples 1-36, wherein the one or more physiological traits are indicative of a systolic blood pressure, and wherein the attribute sign defines at least one of a maximum systolic blood pressure for the obstetric condition or a minimum systolic blood pressure for the obstetric condition.

Example 38: The system of any of examples 1-37, wherein the one or more physiological traits are indicative of a diastolic blood pressure, and wherein the attribute sign defines at least one of a maximum diastolic blood pressure for the obstetric condition or a minimum diastolic blood pressure for the obstetric condition.

Example 39: The system of any of examples 1-38, wherein the one or more physiological traits are indicative of an oxygen saturation level, and wherein the attribute sign defines at least one of a maximum oxygen saturation level for the obstetric condition or a minimum oxygen saturation level for the obstetric condition.

Example 40: The system of any of examples 1-39, wherein the one or more physiological traits are indicative of a respiration rate, and wherein the attribute sign defines at least one of a maximum respiration rate for the obstetric condition or a minimum respiration rate for the obstetric condition.

Example 41: The system of any of examples 1-40, wherein the one or more physiological traits are indicative of an activity level, and wherein the attribute sign defines at least one of a maximum activity level for the obstetric condition or a minimum activity level for the obstetric condition.

Example 42: The system of any of examples 1-41, wherein the one or more physiological traits are indicative of a fluid level, and wherein the attribute sign defines at least one of a maximum fluid level for the obstetric condition or a minimum fluid level for the obstetric condition.

Example 43: The system of any of examples 1-42, wherein the one or more physiological traits are indicative of a blood glucose level, and wherein the attribute sign defines at least one of a maximum blood glucose level for the obstetric condition or a minimum blood glucose level for the obstetric condition.

Example 44: The system of any of examples 1-43, wherein the one or more physiological traits are indicative of a weight, and wherein the attribute sign defines at least one of a maximum weight for the obstetric condition or a minimum weight for the obstetric condition.

Example 45: The system of any of examples 1-44, wherein the one or more physiological traits includes an electrocardiogram, and wherein the one or more sensors are configured to sense the electrocardiogram.

Example 46: The system of any of examples 1-45, wherein the one or more physiological traits includes an echocardiogram, and wherein the one or more sensors are configured to sense the echocardiogram.

Example 47: The system of any of examples 1-46, wherein the one or more physiological traits includes a body temperature, and wherein the one or more sensors are configured to sense the temperature.

Example 48: The system of any of examples 1-47, wherein the one or more physiological traits includes a muscle contraction, and wherein the one or more sensors are configured to sense the muscle contraction.

Example 49: The system of any of examples 1-48, wherein the one or more physiological traits includes an audible sound, and wherein the one or more sensors are configured to sense the audible sound.

Example 50: The system of any of examples 1-49, wherein the one or more sensors are configured to sense an accelerometer motion caused by a physical movement of the patient.

Example 51: The system of any of examples 1-50, wherein the one or more sensors are configured to sense an electromyograph signal of the patient.

Example 52: The system of any of examples 1-51, wherein the one or more sensors are configured to sense an oxygen saturation signal of the patient.

Example 53: The system of any of examples 1-52, wherein the one or more sensors are configured to sense an optical signal influenced by the patient.

Example 54: The system of any of examples 1-53, wherein the one or more sensors are configured to sense an arterial tonometry signature of the patient.

Example 55: The system of any of examples 1-54, wherein the one or more sensors are configured to sense a force exerted by a weight of the patient.

Example 56: The system of any of examples 1-55, wherein the one or more sensors are configured to sense a blood glucose level of the patient.

Example 57: The system of any of examples 1-56, wherein the attribute sign is indicative of a miscarriage of the patient.

Example 58: The system of any of examples 1-57, wherein the processing circuitry is configured to: define one or more first patient attributes using one or more received output signals indicative of at least one of a first fertility phase of the patient, a first pregnancy of the patient, a first labor of the patient, or a first post-partum condition of the patient; and define one or more second patient attributes using one or more received output signals indicative of at least one of a second fertility phase of the patient, a second pregnancy of the patient, a second labor of the patient, or a second post-partum condition of the patient.

Example 59: A method, comprising: sensing one or more physiological traits indicative of one or more patient attributes of a patient using one or more sensors, wherein the one or more patient attribute is indicative of one or more physiological characteristics of a body of the patient; receiving, by processing circuitry, one or more output signals generated by sensing circuitry operably connected to the one or more sensors, wherein the one or more output signals are indicative of the one or more patient attributes, defining, using the processing circuitry, the one or more patient attributes using the one or more received output signals, and issuing a communication, using the processing circuitry, based on a comparison of the one or more patient attributes and an attribute sign, wherein the attribute sign defines a threshold for the patient attribute, wherein the attribute sign is indicative of an obstetric condition defined by the one or more of the physiological characteristics, and wherein the obstetric condition is indicative of a fertility phase of the patient, a pregnancy of the patient, labor of the patient, or a post-partum condition of the patient.

Example 60: The method of example 59, further comprising: sensing, using the one or more sensors, a plurality of physiological traits indicative of a plurality of physiological characteristics, receiving, by the processing circuitry, the one or more output signals, wherein the one or more output signals is indicative of the plurality of physiological traits, defining, using the processing circuitry, a plurality of patient attributes using the one or more received output signals, issuing, using the processing circuitry, the communication based on a comparison of the plurality of patient attributes and the attribute sign, wherein the attribute sign is indicative of an obstetric condition defined by the plurality of physiological characteristics.

Example 61: The method of example 59 or 60, further comprising sensing, using the one or more sensors, a first physiological trait indicative of a first attribute and a second physiological trait indicative of a second attribute, wherein the patient attribute is based on at least the first attribute and the second attribute.

Example 62: The method of any of examples 59-61, wherein the one or more output signals includes a first output signal from first sensing circuitry of a first sensor and a second output signal from second sensing circuitry of a second sensor, and further comprising defining, using the processing circuitry, the one or more patient attributes using the first output signal and the second output signal.

Example 63: The method of any of examples 59-62, wherein the patient attribute at least one of a temperature, a hormone level, a muscle contraction, a heart rate, a systolic blood pressure, a diastolic blood pressure, an oxygen saturation level, a respiration rate, a blood glucose level, or a weight.

Example 64: The method of any of examples 59-63, further comprising: generating, using the processing circuitry, a plurality of patient attributes as the processing circuitry receives the one or more output signals, and comparing, using the processing circuitry, the plurality of patient attributes to the attribute sign.

Example 65: The method of any of examples 59-64, further comprising communicating, using the processing circuitry, the communication to device circuitry of at least one of a patient input/output device, an external device, or a clinician IO device to cause at least one of the patient input/output device, the external device, or the clinician IO device to provide an output sensible by the maternal patient, a clinician, or another user when the processing circuitry issues the communication.

Example 66: The method of any of examples 59-65, further comprising communicating, using the processing circuitry, data indicative of at least one of the one or more physiological traits, a patient physiological parameter indicative of the one of the one or more physiological traits, or the patient attribute, to device circuitry of at least one of a patient input/output device, an external device, or a clinician IO device.

Example 67: The method of any of examples 59-66, further comprising: generating, using the processing circuitry, a plurality of patient attributes as the processing circuitry receives the one or more output signals, and defining, using the processing circuitry, the attribute sign using the plurality of patient attributes.

Example 68: The method of any of examples 59-67, further comprising selecting, using the processing circuitry, one or more treatment recommendations based on the communication.

Example 69: The method of example 68, further comprising communicating, using the processing circuitry, the treatment recommendations to device circuitry mechanically supported by a patient input/output device to cause the patient input/output device to provide an output sensible by the patient, a clinician, or another user indicative of the treatment recommendations.

Example 70: The method of any of examples 59-69, further comprising communicating, using the processing circuitry, a tier I patient communication based on a comparison of the patient attribute and a first attribute sign or a tier II patient communication based on a comparison of the patient attribute and a second attribute sign.

Example 71: The method of any of examples 59-70, further comprising comparing, using the processing circuitry, the patient attribute to the attribute sign using a machine learning algorithm.

Example 72: The method of example 71, further comprising: receiving, by the processing circuitry, an input from a clinician input/output device, wherein the input is indicative of an assessed risk to the patient when the processing circuitry issued a previously issued communication and a previously defined patient attribute, and training, using the processing circuitry, the machine learning algorithm using a training data set indicative of the previously defined patient attribute and the indicative input.

Example 73: The method of example 72, further comprising, using the processing circuitry, updating the training set of the machine learning algorithm based on the patient attribute.

Example 74: The method of example 72 or example 73, further comprising updating, using the processing circuitry, the training set of the machine learning algorithm based on the indicative input.

Example 75: The method of any of examples 59-74, further comprising: receiving, using the processing circuitry, an input from a clinician input/output device, wherein the input is indicative of an assessed risk to the patient when the processing circuitry issued a previously issued communication and a previously defined patient attribute, and defining, using the processing circuitry, the attribute limit using a machine learning algorithm, wherein the machine learning algorithm is trained using a training data set indicative of the previously defined patient attribute and the indicative input.

Example 76: The method of any of examples 59-75, further comprising defining, using the processing circuitry, the attribute sign using a machine learning algorithm, wherein the machine learning algorithm is trained using population attributes sensed from a population of other patients.

Example 77: The method of any of examples 59-76, wherein: the one or more physiological traits include one or more fetal physiological traits indicative of one or more fetal attributes of a fetal patient carried by the patient, the one or more fetal attributes are indicative of one or more physiological characteristics of the fetal patient, the one or more patient attributes includes the one or more fetal attributes, and the attribute sign is indicative of an obstetric condition defined by the one or more physiological characteristics of the fetal patient.

Example 78: The method of example 77, wherein the one or more output signals is a mixed output signal indicative of the one or more physiological traits including the one or more fetal physiological traits, and further comprising defining, using the processing circuitry, the one or more fetal attributes using the mixed output signal.

Example 79: The method of any of examples 59-78, wherein the patient attribute is indicative of a body temperature and the attribute sign defines one of a maximum temperature for the obstetric condition or a minimum temperature for the obstetric condition.

Example 80: The method of any of examples 59-79, wherein the patient attribute is indicative of a hormone level and the attribute sign defines one of a maximum hormone level for the obstetric condition or a minimum hormone level for the obstetric condition.

Example 81: The method of any of examples 59-80, wherein the patient attribute is indicative of a muscle contraction, and wherein the attribute sign defines one of a maximum muscle contraction for the obstetric condition or a minimum muscle contraction level for the obstetric condition.

Example 82: The method of any of examples 59-81, wherein the patient attribute is indicative of a heart rate, and wherein the attribute sign defines one of a maximum heart rate for the obstetric condition or a minimum heart rate for the obstetric condition.

Example 83: The method of any of examples 59-82, wherein the patient attribute is indicative of a systolic blood pressure, and wherein the attribute sign defines one of a maximum systolic blood pressure for the obstetric condition or a minimum systolic blood pressure for the obstetric condition.

Example 84: The method of any of examples 59-83, wherein the patient attribute is indicative of a diastolic blood pressure, and wherein the attribute sign defines one of a maximum diastolic blood for the obstetric condition or a minimum diastolic blood pressure for the obstetric condition.

Example 85: The method of any of examples 59-84, wherein the patient attribute is indicative of an oxygen saturation level, and wherein the attribute sign defines one of a maximum oxygen saturation level for the obstetric condition or a minimum oxygen saturation level for the obstetric condition.

Example 86: The method of any of examples 59-85, wherein the patient attribute is indicative of a respiration rate, and wherein the attribute sign defines one of a maximum respiration rate for the obstetric condition or a minimum respiration rate for the obstetric condition.

Example 87: The method of any of examples 59-86, wherein the patient attribute is indicative of an activity level, and wherein the attribute sign defines one of a maximum activity level for the obstetric condition or a minimum activity level for the obstetric condition.

Example 88: The method of any of examples 59-87, wherein the patient attribute is indicative of a blood glucose level, and wherein the attribute sign defines one of a maximum blood glucose level for the obstetric condition or a minimum blood glucose level for the obstetric condition.

Example 89: The method of any of examples 59-88, wherein the patient attribute is indicative of a weight, and wherein the attribute sign defines one of a maximum weight for the obstetric condition or a minimum weight for the obstetric condition.

Example 90: The method of any of examples 59-89, wherein the patient attribute is indicative of a fluid level, and wherein the attribute sign defines one of minimum fluid level for the obstetric condition or a maximum fluid level for the obstetric condition.

Example 91: The method of any of examples 59-90, wherein the patient physiological trait is at least one of an electrocardiogram, an echocardiogram, an audible sound, an accelerometer signal indicative of a movement of the patient, an electromyography signal indicative of a muscle contraction of the patient, an oxygen saturation signal indicative of an oxygen saturation of the patient, or an optical signal influenced by the body of the patient.

Example 92: The method of any of examples 59-91, further comprising:

sensing one or more first physiological traits during at least one of a first fertility phase of the patient, a first pregnancy of the patient, a first labor of the patient, or a first post-partum condition of the patient; and sensing one or more second physiological traits during at least one of a second fertility phase of the patient, a second pregnancy of the patient, a second labor of the patient, or a second post-partum condition of the patient.

Example 93: The method of any of examples 59-92, wherein the attribute sign is indicative of a miscarriage of the patient.

Example 94: A system comprising processing circuitry configured to perform the method of any one or more of examples 59-93.

Example 95: A non-transitory computer readable storage medium comprising program instructions configured to cause processing circuitry to perform the method of any one or more of examples 59-93.

Example 96: A system comprising: one or more sensors configured in an implantable medical device and configured to sense one or more physiological traits indicative of one or more patient attributes of a patient, wherein the one or more patient attributes are indicative of one or more physiological characteristics of a body of the patient; sensing circuitry operably connected to the one or more sensors and configured to issue one or more output signals indicative of the one or more physiological traits; and processing circuitry operably connected to the sensing circuitry, wherein the processing circuitry is configured to: determine an attribute sign that is indicative of an obstetric condition defined by the one or more of the physiological characteristics, wherein the obstetric condition is indicative of a fertility phase of the patient, a pregnancy of the patient, labor of the patient, or a post-partum condition of the patient, and generate an output based at least in part on the attribute sign that is indicative of the obstetric condition defined by the one or more of the physiological characteristics.

Example 97: The system of example 96, wherein the implantable medical device comprises an insertable cardiac monitor, the insertable cardiac monitor comprising a distal electrode, a proximal electrode, and circuitry comprising a processer within the housing, the circuitry configured to sense the one or more physiological traits indicative of one or more patient attributes of a patient.

Example 98: The system of example 96 comprising any of the foregoing system examples, wherein the one or more sensors configured in the implantable medical device to sense the one or more physiological traits indicative of one or more patient attributes of a patient are included in an insertable cardiac monitor, the insertable cardiac monitor comprising a distal electrode, a proximal electrode, and circuitry comprising a processer within the housing, the circuitry configured to sense the one or more physiological traits indicative of one or more patient attributes of a patient.

Various examples have been described. These and other examples are within the scope of the following claims.

What is claimed is:

1. A system comprising:

one or more sensors configured to sense a first physiological trait indicative of a first physiological characteristic of a body of a patient and a second physiological trait indicative of a second physiological characteristic of the body of the patient;

sensing circuitry operably connected to the one or more sensors, the sensing circuitry configured to issue a first electrical output signal indicative of the first physiological trait and a second electrical output signal indicative of the second physiological trait;

processing circuitry operably connected to the sensing circuitry, wherein the processing circuitry is configured to:

receive the first electrical output signal and the second electrical output signal from the sensing circuitry;

define a patient attribute based on the received first electrical output signal and the received second electrical output signal, wherein the patient attribute is indicative of a third physiological characteristic of the body of the patient;

issue a communication based on a comparison of the patient attribute and an attribute sign, wherein the attribute sign includes a threshold for the patient wherein the attribute sign is indicative of an obstetric condition defined by the third physiological characteristic, and wherein the obstetric condition is indicative of a fertility phase of the patient, a pregnancy of the patient, labor of the patient, or a post-partum condition of the patient;

wherein the one or more sensors is configured to sense a fourth physiological trait indicative of a fourth physiological characteristic of the body of the patient, wherein the sensing circuitry is configured to issue a third output electrical signal indicative of the fourth physiological trait, and wherein the processing circuitry is configured to:

determine an updated obstetric condition of the patient; and cause the one or more sensors to sense the fourth physiological trait indicative of the fourth physiological characteristic of the body of the patient, wherein the fourth physiological trait is based on the updated obstetric condition and is different from the first physiological trait and from the second physiological trait.

2. The system of claim 1, wherein:
the processing circuitry is configured to define a second patient attribute using the first received output signal or the second received output signal, and
the processing circuitry is configured to issue the communication further based on a comparison of the second patient attribute and the attribute sign.

3. The system of claim 1, wherein the patient attribute is a heart rate, a hormone level, a temperature, a systolic blood pressure, a diastolic blood pressure, an oxygen saturation level, a respiration rate, a muscle contraction, a blood glucose level, a weight, an activity level, or a fluid level.

4. The system of claim 1, wherein the processing circuitry is configured to define the patient attribute based on the obstetric condition.

5. The system of claim 1, wherein the processing circuitry is configured to receive an indication of the obstetric condition from a user input device.

6. The system of claim 1, wherein the processing circuitry is configured to direct the one or more sensors to sense the first physiological trait or the second physiological trait based on the obstetric condition.

7. The system of claim 1, wherein the processing circuitry is configured to identify the obstetric condition based on the comparison of the patient attribute and the attribute sign.

8. The system of claim 1, wherein the processing circuitry is configured to issue the communication to device circuitry of at least one of a patient input/output device, a clinician input/output device, or an external device to cause the patient input/output device, the clinician input/output device, or the external device to provide an output sensible by the patient, a clinician, or another user when the processing circuitry issues the communication.

9. The system of claim 1, wherein the processing circuitry is configured to communicate physiological data indicative of at least one of the first physiological trait and the second physiological trait of the patient attribute to device circuitry of at least one of a patient input/output device, a clinician input/output device, or an external device.

10. The system of claim 1, further comprising a medical device configured to contact a body of the patient, wherein the medical device mechanically supports the sensor and at least some portion of the sensing circuitry.

11. The system of claim 1, wherein the processing circuitry is configured to:
select treatment recommendations based on the comparison of the patient attribute and the attribute sign, and
communicate the treatment recommendations to device circuitry mechanically supported by a patient input/output device to cause the patient input/output device to provide an output sensible by the patient, a clinician, or another user indicative of the treatment recommendations.

12. The system of claim 1,
wherein the attribute sign is one of a first attribute sign for the obstetric condition or a second attribute sign for the obstetric condition, wherein the first attribute sign is different from the second attribute sign, and
wherein the processing circuitry is configured to issue a tier I patient communication based on a comparison of the patient attribute and the first attribute sign and issue a tier II patient communication based on a comparison of the patient attribute and the second attribute sign.

13. The system of claim 1, wherein the processing circuitry is configured to determine that the patient has changed from one of the obstetric condition to another one of the obstetric conditions based on the patient attribute.

14. The system of claim 1, wherein the obstetric condition is indicative of a post-partum condition of the patient.

15. The system of claim 1, wherein the one or more sensors are configured in an implantable medical device.

16. A system comprising:
one or more sensors configured to sense a first physiological trait indicative of a first physiological characteristic of a body of a patient and a second physiological trait indicative of a second physiological characteristic of the body of the patient;
sensing circuitry operably connected to the one or more sensors, the sensing circuitry configured to issue a first electrical output signal indicative of the first physiological trait and a second electrical output signal indicative of the second physiological trait;
processing circuitry operably connected to the sensing circuitry, wherein the processing circuitry is configured to:
receive the first electrical output signal and the second electrical output signal from the sensing circuitry;
define a patient attribute based on the received first electrical output signal and the received second electrical output signal, wherein the patient attribute is indicative of a third physiological characteristic of the body of the patient;
compare the patient attribute and an attribute sign, and
issue a communication based on a comparison of the one or more patient attributes attribute and an attribute sign to device circuitry of at least one of a patient input/output device, a clinician input/output device, or an external device,
wherein the attribute sign includes a threshold for the patient attribute,
wherein the attribute sign is indicative of an obstetric condition defined by the third physiological characteristic, and
wherein the obstetric condition is indicative of a fertility phase of the patient, a pregnancy of the patient, labor of the patient, or a post-partum condition of the patient;
wherein the one or more sensors is configured to sense a fourth physiological trait indicative of a fourth physiological characteristic of the body of the patient,
wherein the sensing circuitry is configured to issue a third output electrical signal indicative of the fourth physiological trait, and
wherein the processing circuitry is configured to:
determine an updated obstetric condition of the patient; and
cause the one or more sensors to sense the fourth physiological trait indicative of the fourth physiological characteristic of the body of the patient, wherein the fourth physiological trait is based on the updated obstetric condition and is different from the first physiological trait and from the second physiological trait.

17. A method for operating processing circuitry, comprising
sensing, using one or more sensors, a first physiological trait indicative of a first physiological characteristic of a body of a patient;
sensing, using the one or more sensors, a second physiological trait indicative of a second physiological characteristic of the body of the patient;

receiving, by the processing circuitry, a first electrical output signal and a second electrical output signal generated by sensing circuitry operably connected to the one or more sensors, defining, using the processing circuitry, a patient attribute based on the received first electrical output signal and the received second electrical output signal, wherein the patient attribute is indicative of a third physiological characteristic of the body of the patient, and issuing a communication, using the processing circuitry, based on a comparison of the patient attributes and an attribute sign, wherein the attribute sign defines a threshold for the patient attribute, wherein the attribute sign is indicative of an obstetric condition defined by the third physiological characteristic, and wherein the obstetric condition is indicative of a fertility phase of the patient, a pregnancy of the patient, labor of the patient, or a post-partum condition of the patient;

sensing, using the one or more sensors, a fourth physiological trait indicative of a fourth physiological characteristic of the body of the patient; and receiving, by the processing circuitry, a third electrical output signal generated by sensing circuitry operably connected to the one or more sensors;

determining, by the processing circuitry, an updated obstetric condition of the patient; and causing the one or more sensors to sense the fourth physiological trait indicative of the fourth physiological characteristic of the body of the patient, wherein the fourth physiological trait is based on the updated obstetric condition and is different from the first physiological trait and from the second physiological trait.

* * * * *